(12) United States Patent
Ben Hamou et al.

(10) Patent No.: US 9,414,823 B2
(45) Date of Patent: Aug. 16, 2016

(54) HOLE-CLOSURE DEVICE

(71) Applicant: Medtronic Vascular Galway Limited, Ballybrit, Galway (IE)

(72) Inventors: Eli Ben Hamou, Netanya (IL); Yossi Tuval, Even Yehuda (IL)

(73) Assignee: Medtronic Ventor Technologies Ltd., Yokneam Elit (IL)

( * ) Notice: Subject to any disclaimer, the term of this patent is extended or adjusted under 35 U.S.C. 154(b) by 323 days.

(21) Appl. No.: 13/788,054

(22) Filed: Mar. 7, 2013

(65) Prior Publication Data

US 2013/0289619 A1 Oct. 31, 2013

Related U.S. Application Data

(60) Provisional application No. 61/637,944, filed on Apr. 25, 2012.

(51) Int. Cl.
*A61B 17/00* (2006.01)

(52) U.S. Cl.
CPC ... *A61B 17/0057* (2013.01); *A61B 2017/00243* (2013.01); *A61B 2017/00592* (2013.01); *A61B 2017/00606* (2013.01); *A61B 2017/00668* (2013.01); *A61B 2017/00867* (2013.01)

(58) Field of Classification Search
CPC ............... A61B 17/0057; A61B 2017/00243; A61B 2017/00592; A61B 2017/00606; A61B 2017/00615; A61B 2017/00668; A61B 2017/00867; A61B 2017/00637; A61B 2017/0641; A61B 2017/00584; A61B 2017/00623; A61B 2017/00632; A61F 2/2427; A61F 2/2436

USPC .......... 606/151, 153, 155, 157, 213, 215, 216
See application file for complete search history.

(56) References Cited

U.S. PATENT DOCUMENTS

| | | | | |
|---|---|---|---|---|
| 5,234,447 A * | 8/1993 | Kaster et al. | ................... | 606/153 |
| 5,893,856 A * | 4/1999 | Jacob et al. | ................... | 606/151 |
| 5,907,893 A * | 6/1999 | Zadno-Azizi et al. | ........... | 29/6.1 |
| 5,964,782 A * | 10/1999 | Lafontaine et al. | ........... | 606/213 |
| 6,113,612 A * | 9/2000 | Swanson et al. | ............. | 623/1.15 |
| 6,346,074 B1 | 2/2002 | Stevens | | |
| 6,401,720 B1 | 6/2002 | Stevens | | |
| 6,527,800 B1 * | 3/2003 | McGuckin, Jr. | . A61B | 17/12109 |
| | | | | 623/1.19 |
| 6,978,176 B2 | 12/2005 | Lattouf | | |
| 7,001,398 B2 | 2/2006 | Carley | | |

(Continued)

FOREIGN PATENT DOCUMENTS

CH WO2010139771 A2 * 12/2010
WO WO2008/141322 11/2008

(Continued)

*Primary Examiner* — Ryan J Severson
*Assistant Examiner* — Christian Knauss

(57) ABSTRACT

Medical devices for closing a hole or holes in a subject's body, such as those related to transapical procedures, are disclosed. The medical devices can include a force-providing portion and a tissue-attachment portion. The medical devices can be configured for multiple positions including at least a constrained position and an unconstrained position. In some embodiments, the medical device may be used on a delivery device or delivery tool. In some embodiments, the force-providing portion can pivot radially outward and the tissue-attachment portion can become more constrained, and the hole can be at least partially closed. In some embodiments, the tissue-attachment portion can include a plurality of pins that assume a hook shape.

13 Claims, 17 Drawing Sheets

(56) References Cited

U.S. PATENT DOCUMENTS

| | | |
|---|---|---|
| 7,070,618 B2 | 7/2006 | Streeter |
| 7,404,824 B1 | 7/2008 | Webler |
| 7,549,983 B2 | 6/2009 | Roue |
| 7,635,386 B1 | 12/2009 | Gammie |
| 2002/0082627 A1* | 6/2002 | Berg et al. .................... 606/155 |
| 2003/0093096 A1* | 5/2003 | McGuckin et al. ........... 606/157 |
| 2005/0085852 A1 | 4/2005 | Ditter |
| 2005/0234508 A1* | 10/2005 | Cummins et al. ............. 606/213 |
| 2005/0240200 A1 | 10/2005 | Bergheim |
| 2005/0283188 A1 | 12/2005 | Loshakove |
| 2006/0052804 A1* | 3/2006 | Mialhe ........................... 606/157 |
| 2006/0058871 A1 | 3/2006 | Zakay |
| 2006/0074484 A1 | 4/2006 | Huber |
| 2006/0155327 A1* | 7/2006 | Briganti et al. ............... 606/213 |
| 2006/0247570 A1 | 11/2006 | Pokorney |
| 2006/0259134 A1* | 11/2006 | Schwammenthal et al. . 623/2.11 |
| 2007/0083231 A1 | 4/2007 | Lee |
| 2007/0083232 A1 | 4/2007 | Lee |
| 2007/0093890 A1 | 4/2007 | Eliasen |
| 2007/0112422 A1 | 5/2007 | Dehdashtian |
| 2007/0255399 A1 | 11/2007 | Eliasen |
| 2007/0265700 A1 | 11/2007 | Eliasen |
| 2008/0065149 A1* | 3/2008 | Thielen et al. ................ 606/213 |
| 2008/0125860 A1 | 5/2008 | Webler |
| 2008/0125861 A1 | 5/2008 | Webler |
| 2008/0215085 A1* | 9/2008 | Whisenant et al. ........... 606/213 |
| 2009/0043382 A1 | 2/2009 | Maurer |
| 2009/0048668 A1 | 2/2009 | Wilson |
| 2009/0240326 A1 | 9/2009 | Wilson |
| 2009/0287183 A1 | 11/2009 | Bishop |
| 2009/0318955 A1 | 12/2009 | Dave |
| 2010/0168778 A1 | 7/2010 | Braido |
| 2010/0198254 A1 | 8/2010 | Schaeffer |
| 2010/0228269 A1 | 9/2010 | Garrison |
| 2010/0234882 A1 | 9/2010 | Wahr |
| 2010/0268253 A1 | 10/2010 | Ahlberg |
| 2010/0274091 A1 | 10/2010 | Rothstein |
| 2011/0071623 A1* | 3/2011 | Finch et al. ................... 623/2.11 |
| 2012/0083832 A1* | 4/2012 | Delaloye et al. .............. 606/213 |
| 2012/0253386 A1* | 10/2012 | Rowe et al. ................... 606/213 |

FOREIGN PATENT DOCUMENTS

| | | |
|---|---|---|
| WO | WO2008/141325 | 11/2008 |
| WO | WO2009/002548 | 12/2008 |
| WO | WO2009/100198 | 8/2009 |
| WO | WO2009/127973 | 10/2009 |

\* cited by examiner

HOLE-CLOSURE DEVICE

RELATED APPLICATIONS

This application claims the benefit of U.S. Provisional Patent Application 61/637,944 filed Apr. 25, 2012. The disclosures of which are herein incorporated by reference in their entirety

BACKGROUND

1. Field

Some embodiments generally relate to medical apparatus. Some embodiments relate to apparatus and methods for closing a hole in a subject

2. Background

In many medical procedures, a hole is pierced through tissue of a subject. This hole may have numerous functions that include providing a way for those treating the subject to perform further work on the subject. For example, in minimally-invasive transapical procedures, a hole is pierced in the apex of the heart and tools are inserted into the subject's heart via the hole. In transatrial procedures, a hole is pierced in the subject's atrium, in order to facilitate the insertion of tools therethrough. In aortic catheterization procedures, a hole is pierced through the subject's aorta, in order to facilitate the insertion of tools (e.g., a cannula) through the aorta. For example, cannulation techniques (such as left-ventricular bypass cannulation) are performed by piercing a hole in the aorta and passing a cannula through the hole. In transfemoral procedures, a hole is pierced through the subject's femoral artery, in order to facilitate the insertion of tools therethrough. Thus, a hole or holes may be pierced in the subject for various reasons and in various locations in the subject's body, including but not limited to the subject's heart. In addition, a hole may exist as a wound, tear, or may occur without being pierced by someone treating a subject. In many cases, purse-string sutures are used to close holes after the completion of the aforementioned procedures and treatments.

BRIEF SUMMARY

In accordance with some embodiments, a hole in a subject is at least partially closed using a hole-closure device. The hole to be closed can occur in various areas, regions, tissues, or parts of a subject. For some embodiments, the hole-closure device is used to close a hole in the apex of the subject's heart subsequent to a transapical procedure having been performed on the subject's heart via the apical hole. Alternatively or additionally, the hole-closure device is used to close a hole in the subject's atrium, aorta, femoral artery, and/or a different portion of the subject's body. The hole-closure device may be delivered to the hole (e.g., the apical hole) or the hole location (which may be near the hole's location or can be the area of an intended hole not yet created), while the hole-closure device is constrained by being disposed on a delivery device and by a sheath that is disposed around the hole-closure device.

The hole-closure device may define a tissue-attachment portion and a force-providing portion disposed proximate the tissue-attachment portion. The hole-closure device may further define additional portions or elements beyond a tissue-attachment portion and a force-providing portion. The hole-closure device may be used on a delivery device. This delivery device may provide a way to secure the hole-closure device in a constrained position for delivery of the hole-closure device to the hole or hole location.

The tissue attachment portion is attached to tissue that surrounds the hole or is proximate the hole location. The delivery device may be retracted with respect to the hole-closure device. In some embodiments when the delivery device is retracted with respect to the hole-closure device, a sheath is removed from around the hole-closure device. In some embodiments, the removal of a sheath causes the proximal end of the force-providing portion to pivot radially-outwardly, causing the tissue that surrounds the hole to move toward a central point of the hole, by constricting the tissue-attachment portion.

In some embodiments, the tissue-attachment portion can be configured, at least when the hole-closure device is constrained by the delivery device, to be shaped as a plurality of distally-facing pins disposed around a longitudinal axis of the hole-closure device. For some embodiments, the pins are configured to assume hook shapes, when the pins are advanced distally with respect to the delivery device. For some embodiments the pins are configured to assume other shapes that would permit attachment of the pins to the hole or hole location. The assumption of the hook shapes or other shapes by the pins facilitates attachment of the pins to the subject, specifically tissue that surrounds the hole. In some embodiments, the force-providing portion is shaped to define a circular cross-section (e.g., by having a generally cylindrical shape) when the delivery device, or in some embodiments the sheath, is disposed around the force-providing portion of the hole-closure device. In some embodiments, the force-providing portion is shaped to define a non-circular cross-section when the sheath is disposed around the force-providing portion of the hole-closure device.

There is therefore provided, in accordance with some embodiments, apparatus for closing a hole in a body of a subject, and for use with a delivery device and a sheath, the apparatus including:

a hole-closure device, the hole-closure device being configured to define a constrained configuration, when the hole-closure device is disposed on the delivery device and covered by the sheath, and an unconstrained configuration, when the delivery device has been retracted with respect to the hole-closure device and the hole-closure device is not covered by the sheath, the hole-closure device including:

a tissue-attachment portion configured, at least when the hole-closure device is in the constrained configuration, to be shaped as a plurality of distally-facing pins disposed around a longitudinal axis of the hole-closure device; and a force-providing portion, coupled to the tissue-attachment portion, and disposed proximally with respect to the tissue-attachment portion, the force-providing portion being configured such that, during a transition of the hole-closure device from the constrained configuration to the unconstrained configuration, a proximal end of the force-providing portion pivots radially-outwardly, the force-providing portion thereby moving the pins toward the longitudinal axis of the hole-closure device.

For some embodiments, the force-providing portion is configured to assume a shape that defines a circular cross-section, when the hole-closure device is in the constrained configuration.

For some embodiments, the force-providing portion is configured to assume a planar shape by pivoting radially-outwardly.

For some embodiments, the tissue-attachment portion includes more than three pins.

For some embodiments, the tissue-attachment portion includes more than 10 pins.

For some embodiments, the tissue-attachment portion includes less than 20 pins.

For some embodiments, the tissue-attachment portion includes less than 15 pins.

For some embodiments, each of the pins when in the distally-facing configuration thereof has a length of 2 mm to 15 mm.

For some embodiments, each of the pins when in the distally-facing configuration thereof has a length of 3 mm to 6 mm.

For some embodiments, each of the pins when in the distally-facing configuration thereof has a length of 8 mm to 12 mm.

For some embodiments, each of the distally-facing pins is configured to assume a hook shape by curving radially outwardly, in response to removal of the sheath from around the distally-facing pin.

For some embodiments, when the pin is in the hooked shape, a length from an end of the pin until a center of a curved portion of the pin is more than 30 percent of a total length of the pin.

For some embodiments, when the pin is in the hooked shape, a length from the end of the pin until a center of a curved portion of the pin is less than 50 percent of the total length of the pin.

For some embodiments, when the hole-closure device is in the constrained configuration, a length of the force-providing portion is greater than 3 mm.

For some embodiments, when the hole-closure device is in the constrained configuration, a length of the force-providing portion is less than 10 mm.

For some embodiments, when the hole-closure device is in the unconstrained configuration, the force-providing portion defines a hole having a diameter of more than 1 mm.

For some embodiments, when the hole-closure device is in the unconstrained configuration, the force-providing portion defines a hole having a diameter of less than 7 mm.

There is additionally provided, in accordance with some embodiments, a method for closing a hole in a body of a subject, including:

delivering to the hole a hole-closure device, the hole-closure device being disposed on a first delivery device and being constrained by a sheath disposed around the hole-closure device, during the delivery of the hole-closure device to the hole, the hole-closure device defining a tissue-attachment portion, and a force-providing portion disposed proximally to the tissue-attachment portion;

attaching to tissue that surrounds the hole, the tissue-attachment portion of the hole-closure device; and subsequently, causing the tissue that surrounds the hole to move toward a center of the hole, by constricting the tissue-attachment portion, by causing a proximal end of the force-providing portion to pivot radially-outwardly, by removing the sheath from the proximal end of the force-providing portion.

For some embodiments, delivering the hole-closure device to the hole includes delivering the hole-closure device, the force-providing portion of the hole-closure device being shaped to define a circular cross-section.

For some embodiments, causing a proximal end of the force-providing portion to pivot radially-outwardly includes causing the force-providing portion to assume a planar shape by pivoting radially-outwardly.

For some embodiments, the tissue-attachment portion includes a plurality of pins disposed around a longitudinal axis of the hole-closure device, attaching to tissue that surrounds the hole, the tissue-attachment portion of the hole-closure device includes attaching the pins of the tissue-attachment portion to the tissue that surrounds the hole, and causing the tissue that surrounds the hole to move toward the center of the hole includes moving the pins toward the longitudinal axis of the hole-closure device.

For some embodiments, the tissue-attachment portion includes more than three pins, and attaching to tissue that surrounds the hole the tissue-attachment portion of the hole-closure device includes attaching the more than three pins of the tissue-attachment portion to the tissue that surrounds the hole.

For some embodiments, the tissue-attachment portion includes more than 10 pins, and attaching to tissue that surrounds the hole, the tissue-attachment portion of the hole-closure device includes attaching the more than 10 pins of the tissue-attachment portion to the tissue that surrounds the hole.

For some embodiments, the tissue-attachment portion includes less than 20 pins, and attaching to tissue that surrounds the hole, the tissue-attachment portion of the hole-closure device includes attaching the less than 20 pins of the tissue-attachment portion to the tissue that surrounds the hole.

For some embodiments, the tissue-attachment portion includes less than 15 pins, and attaching to tissue that surrounds the hole, the tissue-attachment portion of the hole-closure device includes attaching the less than 15 pins of the tissue-attachment portion to the tissue that surrounds the hole.

For some embodiments, attaching the pins of the tissue-attachment portion to the tissue that surrounds the hole includes causing the pins to assume hook shapes by curving radially outwardly by removing the sheath from around the pins.

For some embodiments, causing the pins to assume hook shapes includes causing the pins to assume shapes such that a length from an end of each of the pins until a center of a curved portion of the pin is more than 30 percent of a total length of the pin.

For some embodiments, causing the pins to assume hook shapes includes causing the pins to assume shapes such that a length from an end of each of the pins until a center of a curved portion of the pin is less than 50 percent of the total length of the pin.

For some embodiments, delivering the hole-closure device to the hole includes delivering the hole-closure device to the hole while the pins are in distally-facing configurations, and while the pins are in the distally-facing configurations, each of the pins has a length of 2 mm to 15 mm.

For some embodiments, attaching the pins of the tissue-attachment portion to the tissue that surrounds the hole includes attaching the pins to tissue that surrounds a hole in an apex of a heart of the subject, and while the pins are in the distally-facing configurations thereof each of the pins has a length of 3 mm to 6 mm.

For some embodiments, attaching the pins of the tissue-attachment portion to the tissue that surrounds the hole includes attaching the pins to tissue that surrounds a hole in aortic tissue of the subject, and while the pins are in the distally-facing configurations thereof each of the pins has a length of 8 mm to 12 mm.

For some embodiments, delivering the hole-closure device to the hole, the hole-closure device being constrained by the sheath includes delivering the hole-closure device, the force-providing portion of the hole-closure device having a length of greater than 3 mm.

For some embodiments, delivering the hole-closure device to the hole, the hole-closure device being constrained by the sheath includes delivering the hole-closure device, the force-providing portion of the hole-closure device having a length of less than 10 mm.

For some embodiments, causing the proximal end of the force-providing portion to pivot radially-outwardly includes causing the force-providing portion to define a hole having a diameter of more than 1 mm.

For some embodiments, causing the proximal end of the force-providing portion to pivot radially-outwardly includes causing the force-providing portion to define a hole having a diameter of less than 7 mm.

For some embodiments, the first delivery device includes a delivery device that defines a lumen, and the method further includes, subsequent to the attachment of the tissue-attachment portion to the tissue that surrounds the hole, performing a procedure via the lumen of the delivery device, and via the hole.

For some embodiments, performing the procedure via the lumen of the first delivery device, and via the hole, includes:

inserting a second delivery device via the lumen of the first delivery device and via the hole, the second delivery device defining a lumen, and performing the procedure via the lumen of the second delivery device.

For some embodiments, the first delivery device defines an inner portion thereof disposed inside the lumen of the first delivery device, the tissue-attachment portion of the hole-closure device being disposed on the inner portion of the delivery device during the delivery of the hole-closure device to the hole, and the method further includes:

subsequent to attaching to the tissue that surrounds the hole the tissue-attachment portion of the hole-closure device, causing the tissue that surrounds the hole to at least partially move toward a center of the hole by removing the inner portion of the delivery device from inside the tissue-attachment portion, performing the procedure via the lumen of the delivery device includes performing the procedure via the lumen of the delivery device subsequent to removing the inner portion of the delivery device from inside the tissue-attachment portion, and removing the sheath from the proximal end of the force-providing portion includes removing the sheath from the proximal end of the force-providing portion subsequent to performing the procedure via the lumen of the delivery device.

There is further provided, in accordance with some embodiments, apparatus for closing a hole in a body of a subject, and for use with a delivery device and a sheath, the apparatus including:

a hole-closure device, the hole-closure device being configured to define a constrained configuration, when the hole-closure device is disposed on the delivery device and covered by the sheath, and an unconstrained configuration, when the delivery device has been removed from the hole-closure device and the hole-closure device is not covered by the sheath, the hole-closure device defining a tissue-attachment portion, and a force-providing portion disposed proximally to the tissue-attachment portion, the tissue-attachment portion of the hole-closure device being configured to be attached to tissue that surrounds the hole, and the force-providing portion being configured to cause the tissue that surrounds the hole to move toward a center of the hole, by constricting the tissue-attachment portion, by causing a proximal end of the force-providing portion to pivot radially-outwardly, by the sheath being removed from the proximal end of the force-providing portion.

There is further provided, in accordance with some embodiments, apparatus for closing a hole in a subject, the apparatus including:

a hole-closure device, the hole-closure device being configured to define a constrained configuration when the hole-closure device is disposed on a delivery device, and a substantially unconstrained configuration when the delivery device has been retracted with respect to the hole-closure device, the hole-closure device comprising:

a tissue-attachment portion comprising, a plurality of distally-facing pins disposed around a longitudinal axis of the hole-closure device, the pins being configured to achieve a first configuration for delivery proximate the hole and a second configuration for attachment to the subject; the plurality of distally facing pins further forming a lumen, and a force-providing portion, proximate the tissue-attachment portion, the force-providing portion being configured such that, a proximal end of the force-providing portion is adapted to pivot radially-outwardly, and thereby the pins at least partially constrict the lumen.

For some embodiments, the apparatus includes, the hole-closure device is on a delivery device.

For some embodiments, the apparatus includes, the force-providing portion is configured to assume a planar shape by pivoting radially-outwardly.

For some embodiments, the apparatus includes, the force-providing portion is configured to assume a frustoconical shape by pivoting radially-outwardly.

For some embodiments, the apparatus includes, the tissue-attachment portion comprising three or more pins.

For some embodiments, the apparatus includes, the tissue-attachment portion comprises less than twenty pins.

For some embodiments, the apparatus includes, each of the pins when in the distally-facing configuration thereof has a length of 2 mm to 15 mm.

For some embodiments, the apparatus includes, the force-providing portion is configured to assume a shape that defines a circular cross-section, when the hole-closure device is in the constrained configuration.

For some embodiments, the apparatus includes, the force-providing portion is configured to prevent the hole-closure device from migrating when the hole-closure device is attached to the subject.

For some embodiments, the apparatus includes, each of the distally-facing pins is configured to assume a hook shape by curving radially outwardly, in response to retraction of the delivery device.

For some embodiments, the apparatus includes, when the pins are in the hooked shape, a length from an end of each pin until a center of a curved portion of each pin is more than 25 percent of a total length of each pin.

For some embodiments, the apparatus includes, each of the distally-facing pins is configured to assume a straight shape, in response to retraction of the delivery device.

For some embodiments, the apparatus includes, the tissue-attachment portion comprises three or more pins;

wherein each of the distally-facing pins is configured to assume a hook shape by curving radially outwardly in response to retraction of the delivery device;

wherein the force-providing portion is configured to assume a shape that defines a circular cross-section when the hole-closure device is in the constrained configuration on the delivery device;

wherein the force-providing portion is configured to assume a planar shape by pivoting radially-outwardly when the delivery device is retracted from the hole-closure device;

wherein the lumen of the tissue-attachment portion constricts when the force-providing portion assumes the planar shape;

wherein the lumen of the tissue-attachment portion constricts toward a center point on the longitudinal axis of the hole-closure device.

For some embodiments, a method for closing a hole in a subject, includes:

delivering a hole-closure device proximate a hole location, the hole-closure device being disposed on a delivery device, and being constrained by the delivery device during the delivery of the hole-closure device proximate the hole, the hole-closure device defining a tissue-attachment portion having three or more pins and a force-providing portion proximate the tissue-attachment portion;

attaching the hole-closure device to tissue that surrounds the hole location; and subsequently retracting the delivery device, causing a proximal end of the force-providing portion to pivot radially-outwardly such that the force-providing portion is substantially unconstrained, wherein the tissue-attachment portion becomes more constrained and causing the tissue that surrounds the hole to move toward a point of the hole.

For some embodiments, the method includes, the tissue-attachment portion having three or more pins is configured such that when the pins are advanced distally the pins assume a hook shape, the method further comprising when the hole-closure device is attached to tissue, at least some the pins of the tissue-attachment portion of the hole-closure device engage with the tissue.

For some embodiments, the method includes, the force-providing portion of the hole-closure device being shaped to define a circular cross-section.

For some embodiments, the method includes, the method further comprising creating a hole and dilating a hole, wherein attaching the hole-closure device to the tissue occurs prior to creating the hole or prior to dilating the hole.

For some embodiments, the method includes, the delivery device further comprises an inner tube and an outer tube;

wherein when the inner tube is retracted the tissue attachment portion of the hole-closure device at least partially constricts, at least partially closing the hole.

For some embodiments, the method includes, the delivery device further comprises a lumen and a sheath, wherein the delivery device defines an inner portion thereof disposed inside the lumen of the delivery device, the tissue-attachment portion of the hole-closure device being disposed on the inner portion of the delivery device during the delivery of the hole-closure device to the hole, the method further comprising performing a procedure via the lumen of the delivery device;

wherein performing the procedure via the lumen of the delivery device comprises performing the procedure via the lumen of the delivery device subsequent to attaching the hole-closure device, wherein subsequent to attaching the hole-closure device, causing the tissue that surrounds the hole to at least partially move toward a center of the hole by retracting the inner portion of the delivery device, and removing the sheath from the proximal end of the force-providing portion; wherein removing the sheath from the proximal end of the force-providing portion comprises removing the sheath from the proximal end of the force-providing portion subsequent to performing the procedure via the lumen.

There is further provided, in accordance with some embodiments, apparatus for closing a hole and for use with a delivery device and a sheath, the apparatus including:

a hole-closure device, the hole-closure device defining a tissue-attachment portion, and a force-providing portion proximate to the tissue-attachment portion, the hole-closure device being configured to define a constrained configuration when the hole-closure device is disposed on the delivery device and covered by the sheath, and an unconstrained configuration when the delivery device has been removed from the hole-closure device and the hole-closure device is not covered by the sheath, the tissue-attachment portion of the hole-closure device being configured to be attached to tissue that surrounds the hole within the subject, and the force-providing portion being configured to pivot radially-outwardly by the sheath being removed from the proximal end of the force-providing portion, wherein the force-providing portion assumes a substantially planar shape;

whereby causing the tissue that surrounds the hole to move inwardly to the center of the hole.

The embodiments and related concepts will be more fully understood from the following detailed description of the embodiments thereof.

DETAILED DESCRIPTION OF EMBODIMENTS

While the disclosure refers to illustrative embodiments for particular embodiments, it should be understood that the disclosure is not limited thereto. Modifications can be made to the embodiments described herein without departing from the spirit and scope of the present disclosure. Those skilled in the art with access to this disclosure will recognize additional modifications, embodiments, and embodiments within the scope of this disclosure and additional fields, in which the disclosed examples could be applied. Therefore, the following detailed description is not meant to be limiting. Further, it is understood that the apparatus and methods described below can be implemented in many different embodiments of hardware. Any actual hardware described is not meant to be limiting. The operation and behavior of the apparatus and methods presented are described with the understanding that modifications and variations of the embodiments are possible.

References to "one embodiment," "an embodiment," "some embodiments," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Figure 1A:
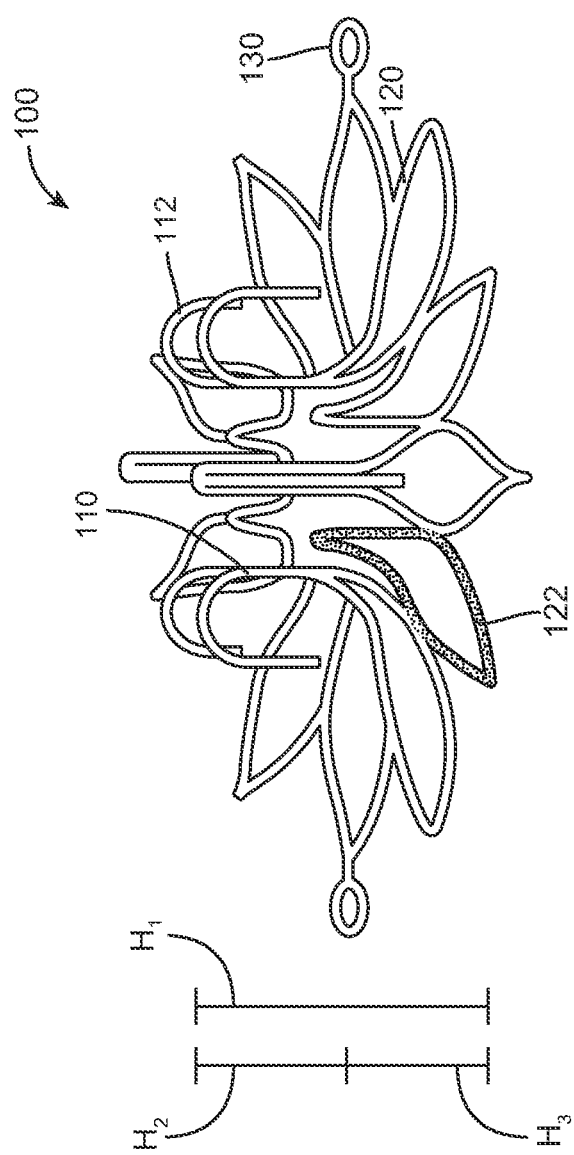
FIGS. 1A-C illustrate a hole-closure device in accordance with some embodiments.
Figure 1B:
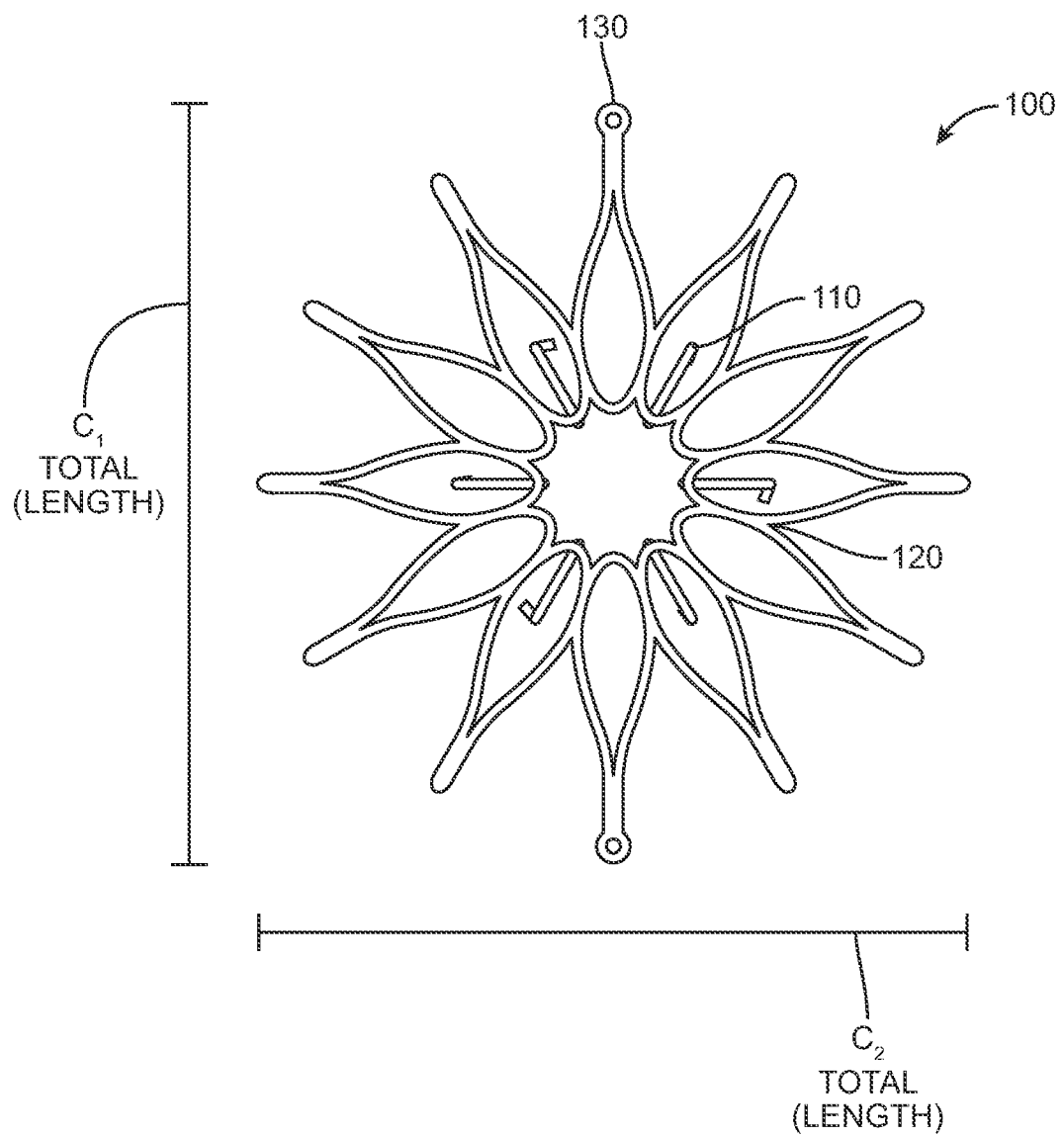
Figure 1C:
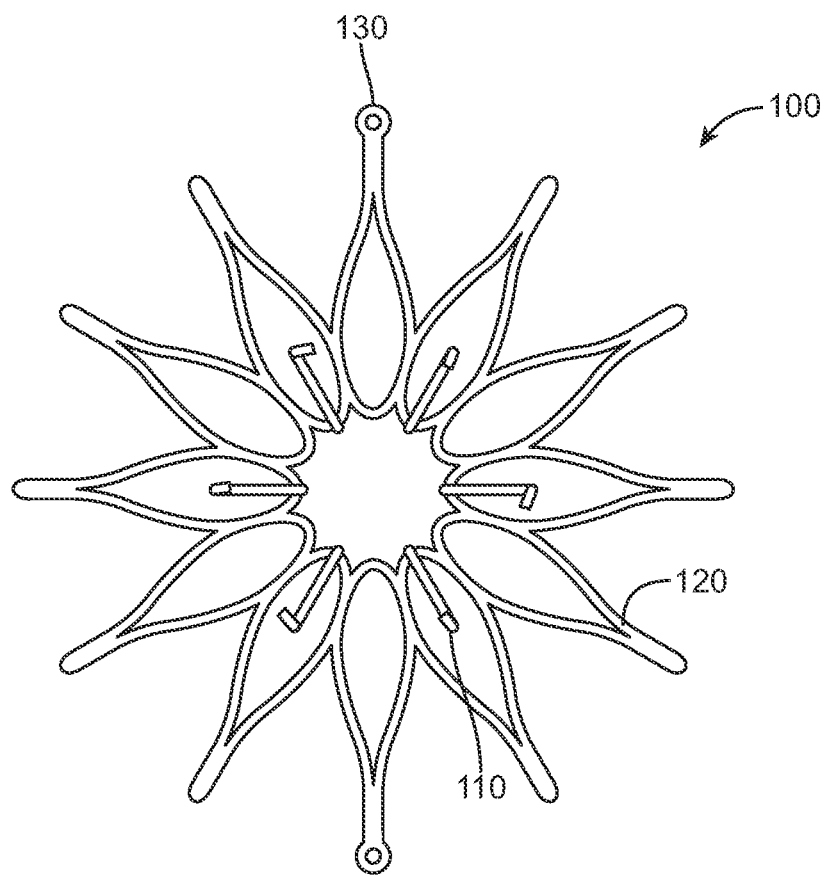

Reference is now made to FIGS. 1A-C, which are schematic illustrations of respective views of a hole-closure device 100, in accordance with some embodiments. FIGS. 1A-C show hole-closure device 100 in an unconstrained configuration. Hole-closure 100 includes at least a tissue-attachment portion 110, and a force-providing portion 120. In some embodiments, tissue-attachment portion 110 may include pins 112. In some embodiments, force-providing portion 120 may include struts 122. In some embodiments, hole-closure device 100 may include attachment element 130.

Hole-closure device 100 is typically used to at least partially close a hole in a subject's body. As described below, tissue-attachment portion 110 is configured to facilitate attachment of the hole-closure device to tissue that surrounds the hole. As used herein, a "hole" may refer to a hole in the subject's body or may also refer to the location of an intended hole not yet created. As described in more detail below, in some embodiments the hole-closure device can be delivered and/or attached prior to the existence of a hole. The hole-closure device 100 can also be attached to the subject prior to a hole existing. This can be done as a preventative measure or out of an abundance of caution so the hole-closure device may be quickly attached and engaged, so that the hole may be at least partially closed quickly if the circumstances warrant this action.

Force-providing portion 120 is configured to cause the hole to at least partially close by constricting the tissue attachment portion 110. In some embodiments the force-providing portion 120 undergoes a transition from a constrained configuration to an unconstrained configuration, as described in further detail below. In other embodiments, the force-providing portion 120 is in a highly constrained position on a delivery device, then transitions to a less constrained position on or off the delivery device, and then further transitions to a substantially unconstrained position or a fully unconstrained position on or off the delivery device.

In some embodiments, the transition of the force-providing portion 120 from a more constrained position to a less constrained position is inversely related to the constrainment of the tissue-attachment portion 110.

FIG. 1A illustrates the hole-closure device 100 in an unconstrained or substantially unconstrained position, in accordance with some embodiments. In some embodiments, in this position the hole-closure device 100 has a total height $H_1$ as illustrated and extends from the bottom of the struts 122 to the top of pins 112. In some embodiments, in this position the tissue-attachment portion 110 of hole-closure device 100 has a height $H_2$ as illustrated and extends from the bottom of the pins 112 to the top of pins 112. In some embodiments, in this position the force-providing portion 120 of hole-closure device 100 has a height $H_3$ as illustrated and extends from the bottom of the struts 122 to the top of struts 122, where the force-providing portion 120 and tissue-attachment portion 110 meet.

In some embodiments, the hole-closure device 100 may include an attachment element 130 for securing some element to the hole-closure device 100. This attachment element 130 could be any means known by one of ordinary skill in the art. For example, in some embodiments as illustrated in FIGS. 1A-C, this attachment element 130 may include a loop to which a wire or other element, including an element of a delivery device, can be secured. In some embodiments, this attachment element 130 can be a clamp, clasp, hook, valve, or any other securing element. In some embodiments, this attachment element 130 may include using an adhesive or additional securing means. In some embodiments, multiple types of attachment elements 130 can be used together for attachment element 130, such as using both an adhesive and a loop. In some embodiments, the hole-closure device 100 has a plurality of attachment elements 130, only one attachment element 130, or no attachment element 130.

FIG. 1B illustrates hole-closure device 100 in an unconstrained or substantially unconstrained position, in accordance with some embodiments. In some embodiments, in this position the hole-closure device 100 has a total length $C_1$ as the length from the attachment element 130 to the other attachment element 130 (as shown in 1B). In other embodiments where no attachment element 130 exist, this total length $C_1$ is the length from the tip of a first strut 122 on one side of hole-closure device 100 to the tip of a second strut 122 opposite the first strut 122 of hole-closure device 100. In some embodiments, in this position the hole-closure device 100 has a total length $C_2$ as the length from the tip of a third strut 122 on one side of hole-closure device 100 to the tip of a fourth strut 122 opposite the third strut 122 of hole-closure device 100. In some embodiments, these distances $C_1$ and $C_2$ may be equal or approximately equal. In some embodiments, these distances $C_1$ and $C_2$ may be of different lengths, such that $C_1$ is less than $C_2$ or such that $C_2$ is less than $C_1$. These differing lengths will cause the hole-closure device 100 (tissue-attachment portion 110 and force-providing portion 120) to be asymmetric.

In some embodiments, pins 112 may be in different orientations on the same hole-closure device 100. In some embodiments, some pins 112 may face away from the longitudinal axis of the hole-closure device 100 while other pins may be turned by varying degrees (such as 90 degrees) so that they are not facing away from the longitudinal axis of the hole-closure device 100 (as illustrated in FIG. 1C). In some embodiments, all of the pins face towards the longitudinal axis of the hole-closure device 100.

FIGS. 1A-C illustrate different shapes of the struts 122 that in some embodiments are included in the force-providing portion 120 of hole-closure device 100. In some embodiments, the struts 122 can be teardrop shape (as shown in FIG. 1B). In other embodiments, the struts may be petal shaped (as discussed with respect to FIGS. 2A-C). In some embodiments, these struts 122 could be many other shapes including circular, square rectangular, triangular, diamond, geometric or non-geometric. In some embodiments, the struts can be alternating shapes or multiple shapes and may be included as part of hole-closure device 100. In some embodiments, there could be an even number of struts 122 of force-providing portion 120. In other embodiments, there could be an odd number of struts 122 of force-providing portion 120.

Figure 2A:
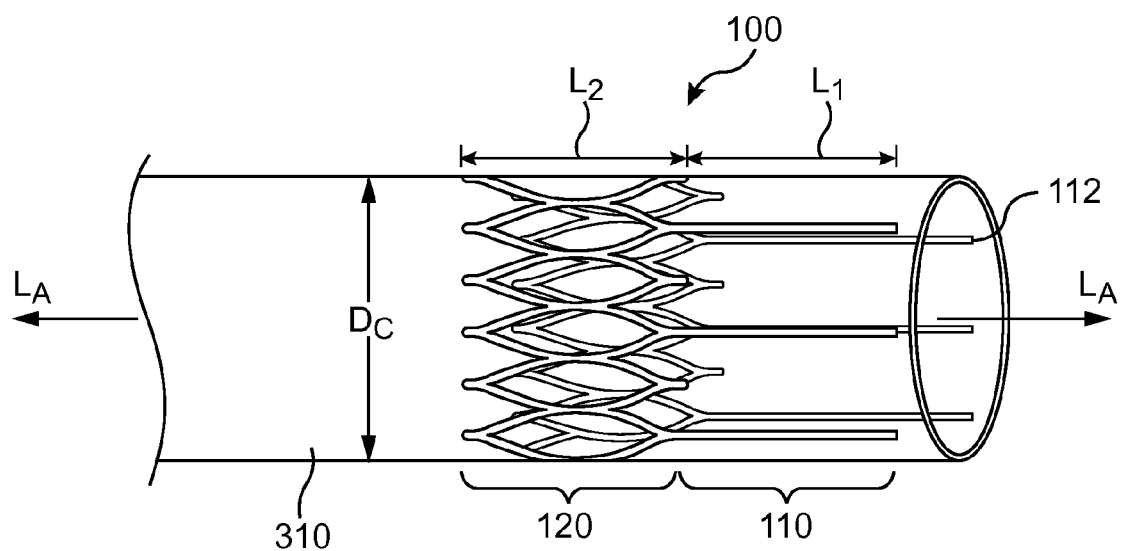
FIGS. 2A-C illustrate a delivery device interacting with a hole closure device in accordance with some embodiments.
Figure 2B:
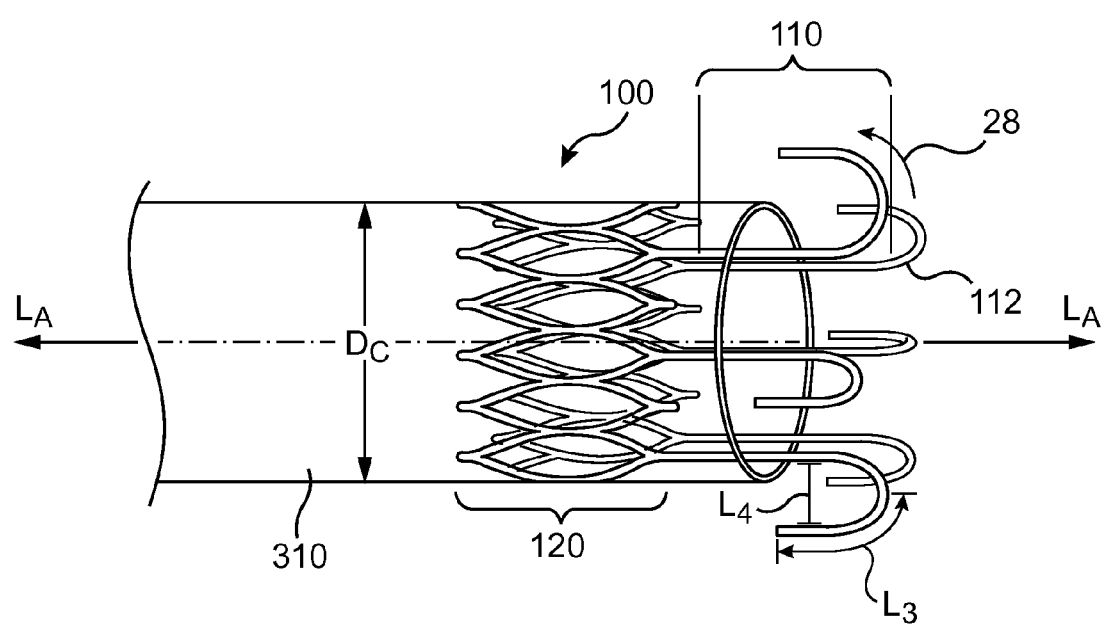
Figure 2C:
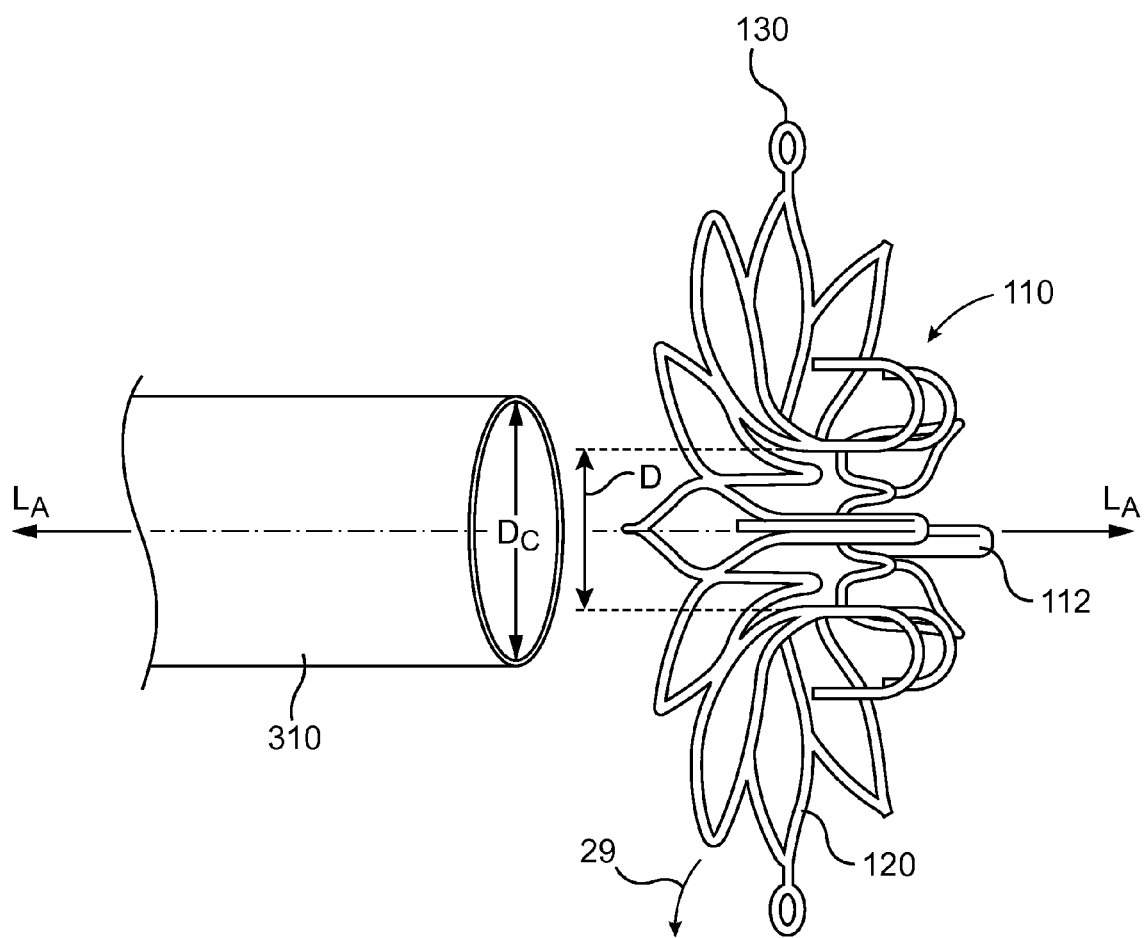

Reference is now made to FIGS. 2A-C, which are schematic illustrations of respective steps of a delivery device 300 being removed from around hole-closure device 100, in accordance with some embodiments. In some embodiments, the delivery device 300 can include a sheath 310. In some embodiments, during delivery of the hole-closure device 100 to a hole 210 in a subject's 200 body (e.g., a hole in the apex of the subject's heart, the subject's atrium, the subject's aorta, the subject's femoral artery, and/or a different portion of the subject's body), hole-closure device 100 is disposed on a delivery device 300, and sheath 310 is disposed around the hole-closure device 100. The delivery device 300 and the sheath 310 thereby maintain hole-closure device 100 in a constrained configuration. For illustrative purposes, FIGS. 2A-C show hole-closure device 100 and sheath 310 in the absence of other parts of the delivery device 300 and the subject's 200 anatomy. In other embodiments, during delivery of the hole-closure device 100 to a hole 210 in a subject's 200 body, hole-closure device 100 is disposed on a delivery device 300 without a sheath 310.

The tissue-attachment portion 110 of the hole-closure device 100 can include any number of tissue-attachment methods. These may include, but are not limited to, pins 112, barbs, posts, adhesives, clamps, or any other suitable method. The tissue-attachment portion may also include combinations of any of these or other suitable methods. Any discussion in this disclosure should not be taken as limiting the tissue-attachment method to a particular method.

As shown in FIG. 2A, for some embodiments, in the constrained configuration of hole-closure device 100, tissue-attachment portion 110 of the device defines a plurality of distally-facing pins 112 (i.e., pins that are disposed parallel to the longitudinal axis of the hole-closure device). In some embodiments, pins 112 are configured to facilitate attachment of the hole-closure device 100 to tissue of the subject that surrounds the hole 210 by being advanced into the subject's tissue. In some embodiments, tissue-attachment portion 110 may include an even number of pins 112. In some embodiments, tissue-attachment portion 110 may include an odd number of pins 112.

As shown in FIG. 2A, the pins 112 have length $L_1$ that is the length from the intersection of the force-providing portion 120 and the tissue-attachment portion 110 to the distal end of the pins 112. As shown in FIG. 2A, the force-providing portion 120 has a length $L_2$ that is the length from base of the force-providing portion 120 to the intersection of the force-providing portion 120 and the tissue-attachment portion 110. These lengths, $L_1$ and $L_2$, or the lengths of the force-providing portion 120 and the tissue-attachment portion 110 respectively, may be of any suitable length and should not be limited by the figures. In some embodiments, length $L_1$ may be greater than length $L_2$. In some embodiments length $L_1$ may be less than length $L_2$. In some embodiments length $L_1$ may be equal to length $L_2$. In some embodiments length $L_1$ may be nearly equal to length $L_2$.

In some embodiments, in the constrained configuration of force-providing portion 120 of hole-closure device 100, length $L_2$ (shown in FIG. 2A) of the force-providing portion 120 is more than 3 mm, and/or less than 10 mm. Further typically, in the unconstrained configuration of force-providing portion 120, the force-providing portion 120 defines a hole 210 having a diameter D (shown in FIG. 2C) of more than 1 mm, and/or less than 7 mm.

In some embodiments, the distally-facing pins 112 may be substantially straight. In other embodiments the pins 112 may be of different geometry. In some embodiments, the pins 112 may be curved, such as the shape of an s-curve. In other embodiments, the pins 112 may be of a zigzag geometry. In other embodiments, the pins 112 may be of other further geometry as one of ordinary skill in the art would appreciate would be acceptable. In some embodiments, the pins may end with a barb or similar tissue fixation element.

In some embodiments the pins 112 may be of uniform cross-sectional area along their length. In some embodiments the pins 112 may be of gradually changing cross-sectional area along their length. In some embodiments the pins 112 may change cross-sectional area in step wise fashion along their length, going from a larger cross-sectional area to a smaller cross-sectional area. In some embodiments the pins 112 may change cross-sectional area in step wise fashion along their length, going from a smaller cross-sectional area to a larger cross-sectional area.

As shown in FIG. 2B, for some embodiments, in response to being advanced distally with respect to the sheath 310, the distal ends of the pins 112 curve radially outwardly (as indicated by arrow 28), such that the pins assume hook shapes. For some embodiments, in response to being advanced distally with respect to the sheath 310, the distal ends of the pins 112 project radially outwardly (as indicated by arrow 28), such that the pins 112 assume a substantially "V" shape. For some embodiments, in response to being advanced distally with respect to the sheath 310, the distal ends of the pins 112 project radially outwardly (as indicated by arrow 28), such that the pins 112 assume a substantially "L" shape. For some embodiments, in response to being advanced distally with respect to the sheath 310, the distal ends of the pins 112 project radially outwardly (as indicated by arrow 28), such that the pins 112 assume another shape, as would be understood by one of ordinary skill in the art to aid in closing a hole 210 in a subject 200.

In some embodiments, in response to being advanced distally with respect to the sheath 310, the distal ends of the pins 112 stay substantially straight and do not assume a hook or otherwise bent shape.

In some embodiments, in response to being advanced distally with respect to the sheath 310, the distal ends of the pins 112 curve radially outwardly (as indicated by arrow 28), such that the pins 112 assume multiple shapes. For example in some embodiments, the pins 112 could assume alternating hook and "V" shapes. In other embodiments, the pins 112 could assume alternating hook and "L" shapes. In some embodiments, the pins 112 could assume any combination or alternating pattern of types or shapes of pins, as understood by one of ordinary skill in the art to be advantageous.

For some embodiments, the assumption of hook shapes by the pins 112 facilitates attachment of the hole-closure device 100 to the tissue, by causing the pins 112 to become embedded in the tissue. For some embodiments, the assumption of "V" shapes by the pins 112 facilitates attachment of the hole-closure device 100 to the tissue, by causing the pins 112 to become embedded in the tissue. For some embodiments, the assumption of "L" shapes by the pins 112 facilitates attachment of the hole-closure device 100 to the tissue, by causing the pins 112 to become embedded in the tissue. For some embodiments, the assumption of other shapes by the pins 112 facilitates attachment of the hole-closure device 100 to the tissue, by causing the pins 112 to become embedded in the tissue. For some embodiments, the assumption of multiple shapes by the pins 112 facilitates attachment of the hole-closure device 100 to the tissue, by causing the pins 112 to become embedded in the tissue.

In other embodiments, in response to being advanced distally with respect to the sheath 310, the distal ends of the pins 112 curve radially inwardly, such that the pins 112 assume hook shapes. In other embodiments, in response to being advanced distally with respect to the sheath 310, the distal ends of the pins 112 curve radially inwardly, such that the pins assume "V" shapes. In other embodiments, in response to being advanced distally with respect to the sheath 310, the distal ends of the pins 112 curve radially inwardly, such that the pins 112 assume "L" shapes. In other embodiments, in response to being advanced distally with respect to the sheath 310, the distal ends of the pins 112 curve radially inwardly, such that the pins 112 assume other shapes.

In some embodiments, the tissue-attachment portion defines more than three pins 112 (e.g., more than ten pins), and/or less than twenty pins 112 (e.g., less than fifteen pins) e.g., ten to fifteen pins. In other embodiments, the tissue-attachment portion 110 defines twenty or more pins 112. In some embodiments, in the distally-facing configuration thereof, each of the pins 112 has a length $L_1$ (shown in FIG. 2A) of more than 2 mm, and/or less than 15 mm. In some embodiments in which hole-closure device 100 is used to close a hole 210 in the apex of the subject's 200 heart, length is between 3 mm and 6 mm. For embodiments, in which hole-closure device 100 is used to close a hole 210 in tissue of the subject's aorta, length $L_1$ is between 8 mm and 12 mm.

In some embodiments, when a pin 112 assumes a hook shape, a length $L_3$ (shown in FIG. 2B) from the end of the pin 112, until the center of the curved portion of the pin 112 is more than 30 percent, and/or less than 50 percent of the total length $L_1$ of the pin 112. When a hook shape (or other shape) occurs a length $L_3$ from the change in concavity of the hook or other identifiable geometry change down to the end of the pin 112 (as indicated by $L_3$ in FIG. 2B). In some embodiments, pins 112 may include a length L4 from the initial pin 112 position to a distance on the hook portion of pin 112 (as illustrated in FIG. 2B).

As shown in FIGS. 2A and 2B, in a constrained configuration of hole-closure device 100 (e.g., when the device is constrained by sheath 310) defines a lumen having a constrained diameter $D_C$ that generally equals the inner diameter of sheath 310, and force-providing portion 120 assumes a shape that defines a circular cross-section (e.g., force-providing portion 120 has a generally cylindrical shape, as illustrated in FIG. 2A), since the force-providing portion is constrained by the sheath 310. In some embodiments, force-providing portion 120 can assume a shape that defines an oval cross section. In some embodiments, force-providing portion 120 can assume a shape that defines a non-circular and non-oval cross section. In some embodiments, force-providing portion 120 can assume a shape that defines a triangular or a rectangular or a square cross section. In some embodiments, force-providing portion 120 can assume a shape that defines a geometric cross section. In some embodiments, force-providing portion 120 can assume a shape defined by the shape of a delivery device 300. For example, in some embodiments, force-providing portion 120 can assume a shape defined by sheath 310 (as shown in FIG. 2B).

As shown in the transition from FIG. 2B to FIG. 2C, in response to the delivery device 300, which may include a sheath 310, being removed from around the hole-closure device 100, the proximal end of the force-providing portion 120 pivots radially outwardly (as illustrated by arrow 29) and the lumen of the hole closure device 100 constricts to an unconstrained diameter D that is less than the constrained diameter $D_C$, as discussed in more detail below. For example, the proximal end of the force-providing portion 120 may pivot radially-outwardly, such that the force-providing portion 120 assumes a substantially planar shape, as shown in FIG. 2C. In some embodiments, the proximal end of the force-providing portion 120 may curve radially-outwardly, such as to cause the force-providing portion 120 to assume a different shape, such as a frustoconical shape, or a shape that defines a surface that is concave in the distal direction or the proximal direction (as illustrated in FIG. 3E). In some embodiments, the force-providing portion 120 may even pivot to a cylindrical shape such that the force-providing portion is substantially or actually parallel to the pin portion.

In some embodiments, the force-providing portion 120 is configured such that in the unconstrained or substantially unconstrained configuration of the hole-closure device 100, the force-providing portion 120 prevents hole-closure device 100 from migrating through the hole 210 in the subject's 200 tissue, by contacting the tissue that surrounds the hole 210. In some embodiments, the force-providing portion 120 is configured such that in the unconstrained or substantially unconstrained configuration of the hole-closure device 100, the force-providing portion 120 prevents the hole-closure device 100 from migrating through the hole 210 in the subject's tissue, by contacting the tissue that surrounds the hole 210.

In some embodiments as shown for instance in a comparison of FIGS. 2B and 2C, the transition of the shape of the force-providing portion 120 is such that it constricts the lumen formed by the tissue-attachment portion 110 from the constrained diameter $D_C$ to an unconstrained, constricted diameter D, and then maintains the lumen formed by the tissue-attachment portion 110 in the constricted configuration. For example as shown in a comparison of FIGS. 2B and 2C, for embodiments in which the tissue-attachment portion 110 defines a plurality of pins 112, the force-providing portion 120 causes the pins 112 to move toward the longitudinal axis $L_A$ of the hole-closure device 100, by the force-providing portion 120 undergoing the transition when unconstrained. In some embodiments, the pins 112 moving toward the longitudinal axis $L_A$ causes the lumen formed by the pins 112 to be constricted. By constricting the lumen formed by the tissue-attachment portion 110, the force-providing portion 120 pulls tissue that surrounds the hole 210 toward the center of the hole 210, thereby at least partially closing the hole 210.

In some embodiments, hole-closure device 100 can be constructed from any number of suitable materials, including a shape-memory alloy. In some embodiments suitable shape-memory alloys include, but are not limited to, nickel-titanium alloys including nitinol or ferromagnetic shape-memory alloys, or many others. Other exemplary suitable materials would include, but not be limited to metals, plastics, polymers, fibers, and many others. In some embodiments these materials could be used in combinations. For example, one portion of the hole-closure device 100 may be made of one material, such as an alloy, and another portion of the hole-closure device 100 may be made of another material. In some embodiments, the hole closure device 100 may be made from bio-resorbable materials. In some embodiments, these different materials could be combined together to form a portion or portions of the hole closure device 100. For example, a metal could be combined with a polymer to form a portion or portions of the hole closure device 100.

In some embodiments, the hole closure device 100 can comprise one unitary piece. In some embodiments, the hole closure device 100 can be made of a plurality of pieces that are then joined, fastened, coupled, connected, or otherwise brought together to create a hole-closure device.

In some embodiments, the unconstrained shape of the hole-closure device 100 is set using shape-setting techniques, including but not limited, types of heat treatment. In other embodiments, shape-setting techniques other than heat treatment may be used. Applicable and suitable shape setting techniques would be appreciated by one of ordinary skill in the art. In some embodiments, the unconstrained shape of the hole-closure device 100 occurs as a result of manufacturing, without requiring shape-setting techniques.

In some embodiments, the hole-closure device 100 is constrained in the constrained configuration of the hole-closure device 100 by placing the hole-closure device 100 on a delivery device 300. In some embodiments, placing the hole-closure device 100 on a delivery device 300 may include covering the hole-closure device 100 with sheath 310.

It is noted that although, in FIGS. 2A-C, tissue-attachment portion 110 is shown having a specific configuration, other embodiments include using a tissue-attachment portion 110 having a different configuration, and that is configured to facilitate attachment of the hole-closure device 100 to tissue that surrounds a hole 210 or hole location in the subject's 200 body. For example, the tissue-attachment portion 110 may define barbs, pins 112, hooks, different geometries, may include an adhesive, or any combination of the features discussed herein or known by one of ordinary skill in the art at the time. As one example, the tissue-attachment portion 110 may include both barbs and adhesive together.

It is noted that although force-providing portion is shown having a specific configuration in FIGS. 2A-C, other embodiments include using a tissue-attachment portion 110 having a different configuration, and that is configured to constrict the tissue-attachment portion 110 by a proximal end of the force-providing portion 120 pivoting radially-outwardly. For example, as described above, in some embodiments the force-providing portion 120 may define a frustoconical shape in the non-constrained configuration of the force-providing portion 120 (as is illustrated in FIG. 3E). In other embodiments, the force-providing portion 120 may define a different shape in the non-constrained configuration of the force-providing portion 120.

Alternatively or additionally to that discussed, the struts 122 of the force-providing portion 120 may define different shapes to those shown in FIGS. 2A-C. In some embodiments, the struts 122 in FIGS. 2A-C embody a petal like shape. In some embodiment, the struts 122 embody a teardrop-like shape (as illustrated in FIG. 1B). However, one of ordinary skill in the art would appreciate any number of different shaped struts 122 of the force-providing portion, including but not limited to circular, oblong, rectangular, geometric, petal, teardrop, non-geometric struts 122, or many others. In some embodiment the struts of the force-providing portion of the hole-closure device could be made of multiple shapes. In some embodiments these struts 122 could be arranged in advantageous patterns or that may alternate.

Reference is now made to FIG. 3A-3E, which illustrate an embodiment of a hole closure device in accordance herewith being delivered using a delivery device 300. These respective figures provide an example of potential respective steps of a transapical procedure. These examples should not be taken to be limiting of the details and alternatives discussed elsewhere. In addition, this example does not limit the embodiments or applications only to cardiac procedures. Further, this example and all others contained within this disclosure should not be limited only to the order discussed, with each of the relevant or applicable steps able to be performed in any order, as would be appreciated by one of ordinary skill in the art.

For this exemplary transapical procedure, the hole-closure device 100 is inserted into apex 210 of a subject's 200 heart, in accordance with some embodiments. For some embodiments, the hole-closure device 100 is delivered to the apex 210 by the hole-closure device being disposed on an inner tube 320 of a delivery device 300 (such as a catheter, cannula, or any other suitable device), wherein the transapical procedure is performed via the inner tube 320 of the delivery device 300. As shown in the embodiment of FIGS. 3A-3D, sheath 310 is disposed around the hole-closure device 100 during the delivery of the hole-closure device to the apex, as described above.

Figure 3A:
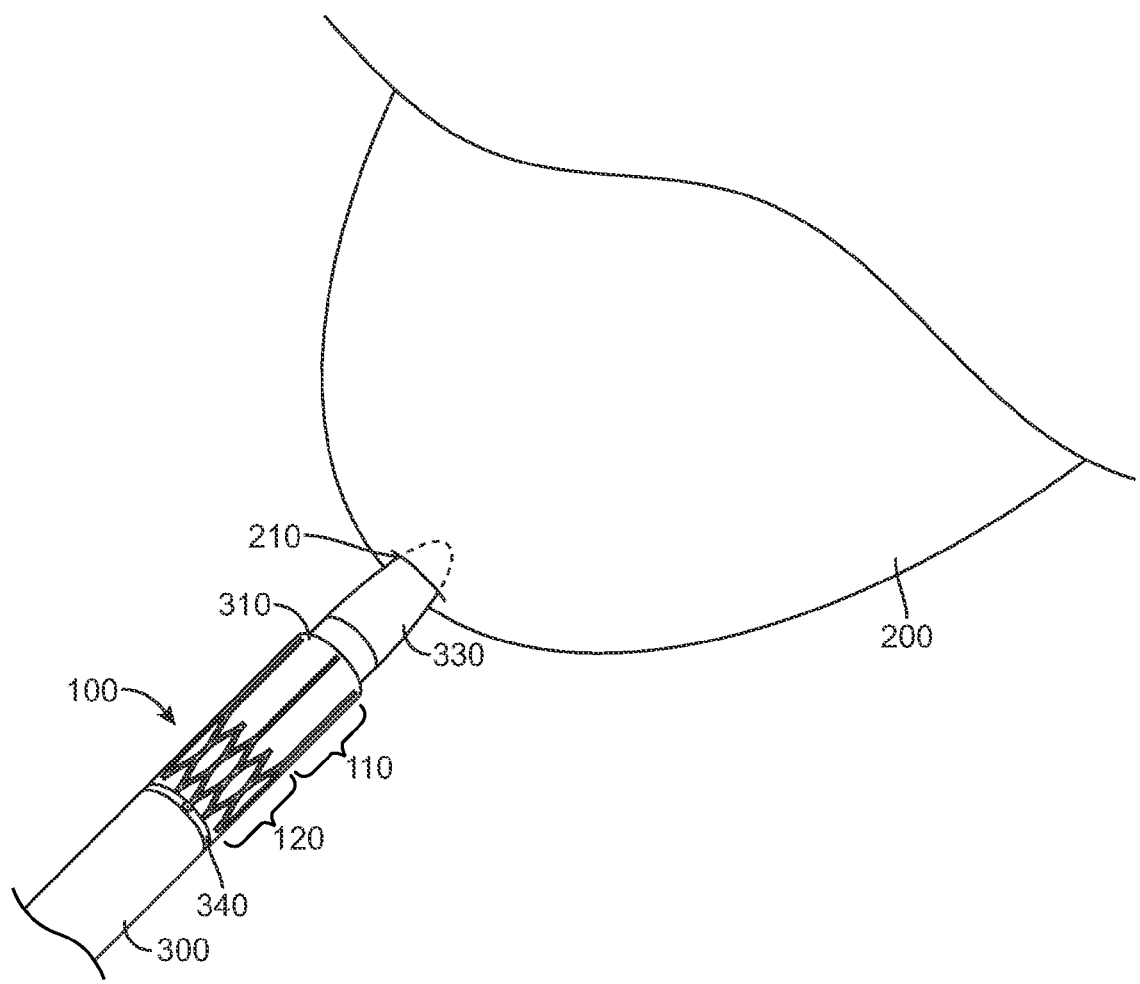
FIGS. 3A-F illustrate a procedure, such as a transapical procedure, during which the hole-closure device is inserted into the apex of a subject's heart, in accordance with some embodiments.
Figure 3B:
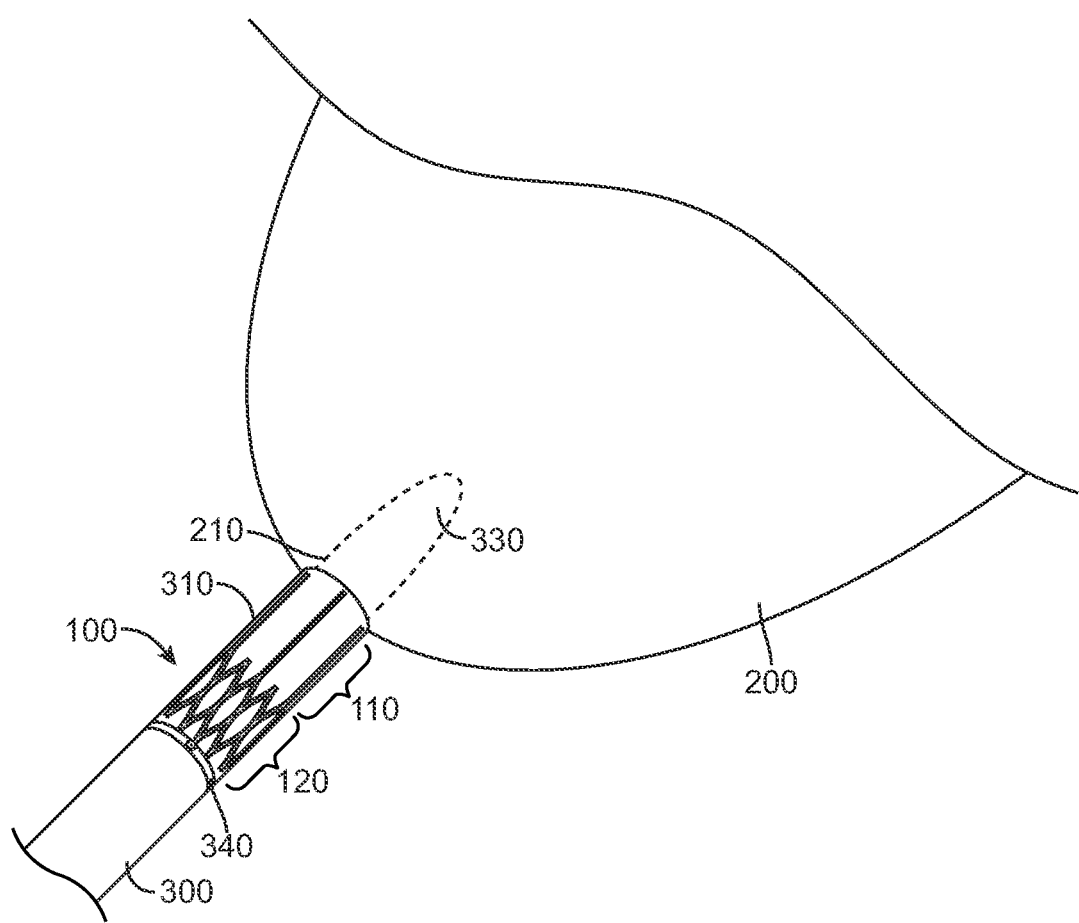

In FIG. 3A a dilator 330 is advanced through apex 210, via delivery device 300, in order to dilate a hole 210. The distal end of the delivery device is advanced such that the distal end is placed against the outer surface of the apex, as shown in FIG. 3B. In some embodiments, tissue-attachment portion 110 of hole-closure device 100 is then advanced distally with respect to the distal end of the delivery device. In some embodiments, this advancing of the tissue-attachment portion 110 can attach the tissue-attachment portion 110 to tissue that surrounds the hole 210.

In some embodiments, an advancing element 340 is used to advance the hole-closure device 100 distally with respect to the delivery device 300, and more particularly with respect to each of the inner tube 320 and the sheath 310. This advancing element 340 can include a plunger or any other suitable means capable of advancing the hole-closure device 100.

Figure 3C:
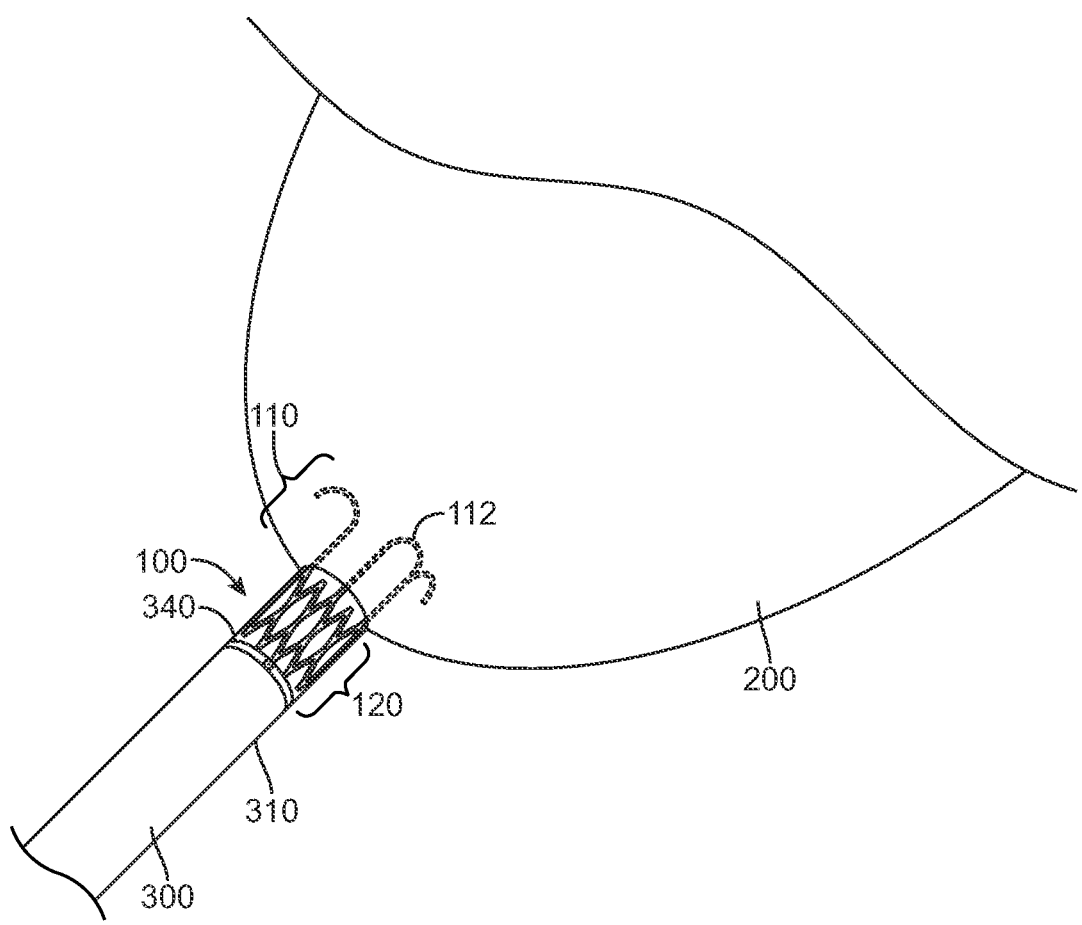

As shown in FIG. 3C, for some embodiments, the tissue-attachment portion 110 defines pins 112, and upon being advanced distally of the sheath 310 and inner tube 320, the distal ends of the pins 112 curve radially outwardly, such that the pins 112 assume hook shapes, the pins 112 thereby becoming embedded in the tissue surrounding the hole 210. As discussed above, these pins 112 can also assume numerous other positions upon being advance distally. In some embodiments not all the pins 112 may become embedded in the tissue surrounding the hole 210. Indeed, in some embodiments having only some pins 112 engage in the tissue surrounding the hole 210 will still cause the hole 210 to at least partially close. In some embodiments, the hole-closure device 100 may be designed with multiple pins 112 such that if only some percentage of the pins 112 engage in the tissue, the hole-closure device 100 can still be effective in at least partially closing the hole 210.

Figure 3D:
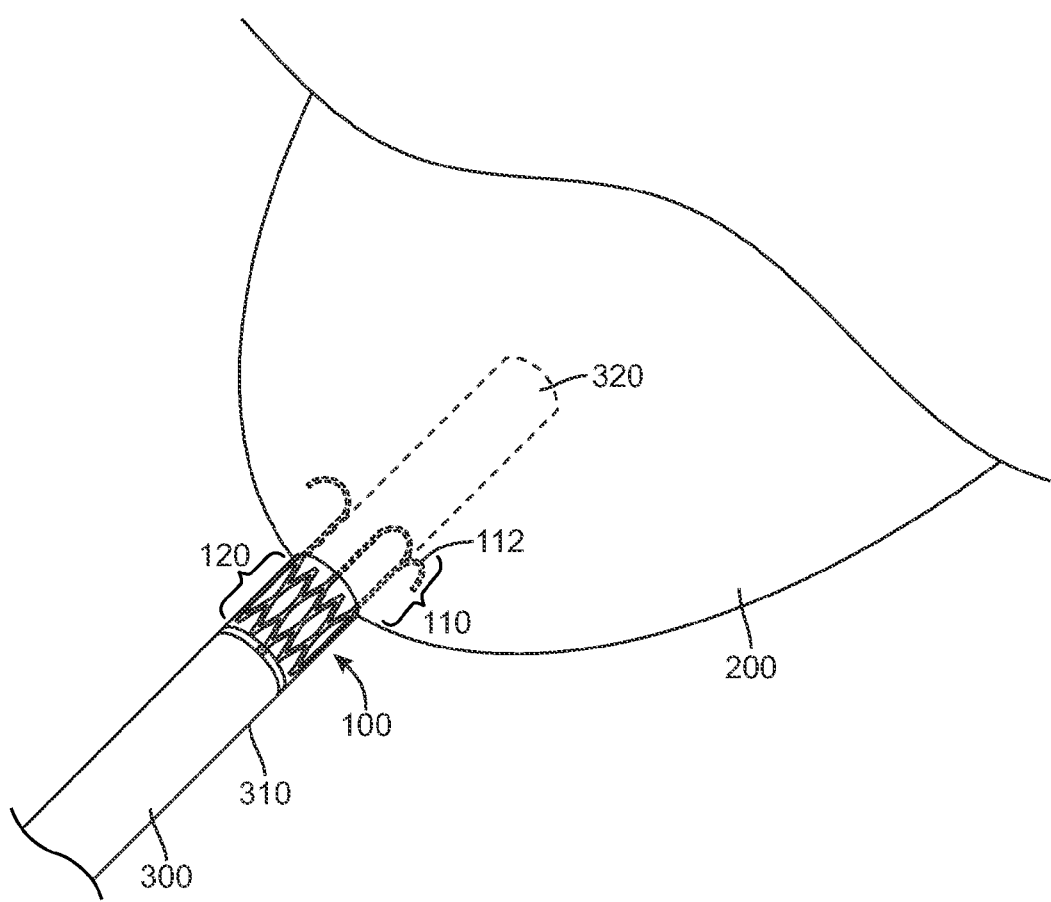
Figure 3E:
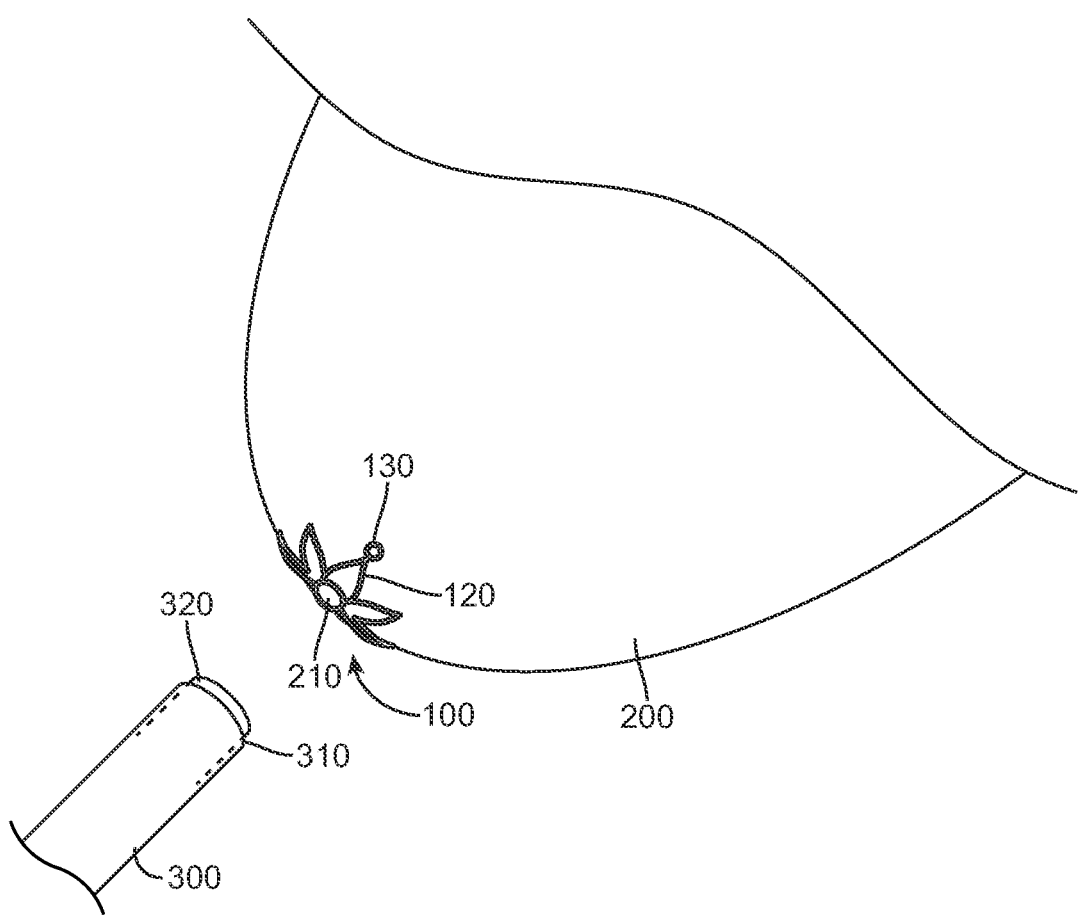

In some embodiments, subsequent to the tissue-attachment portion 110 of the hole-closure device 100 having been attached to the tissue that surrounds the hole 210, the delivery device 100 is advanced through the hole 210 as shown in FIG. 3D, and a transapical procedure is performed via the inner tube 320 of the delivery device, which may be advanced into the heart as shown in FIG. 3D. For example, in some embodiments the transapical procedure may be transapical mitral valve replacement, transapical mitral valve repair, transapical aortic valve replacement, transapical aortic valve repair, left ventricular bypass, aortic cannulation, and/or transapical treatment of a septal defect may be performed via the delivery device. In other embodiments, any type of procedure relevant to the hole 210 and tissue location may be performed via the inner tube 320 of the delivery device 300, including those performed outside the heart.

In some embodiments, subsequent to the transapical procedure having been performed, delivery device 300 is retracted from the subject's 200 heart. In some embodiments, the delivery device 300 is then retracted with respect to force-providing portion 120 of hole-closure device 100. In some embodiments the delivery device 300 and sheath 310 are then retracted with respect to force-providing portion 120 of hole-closure device 100, as shown in FIG. 3E.

Figure 3F:
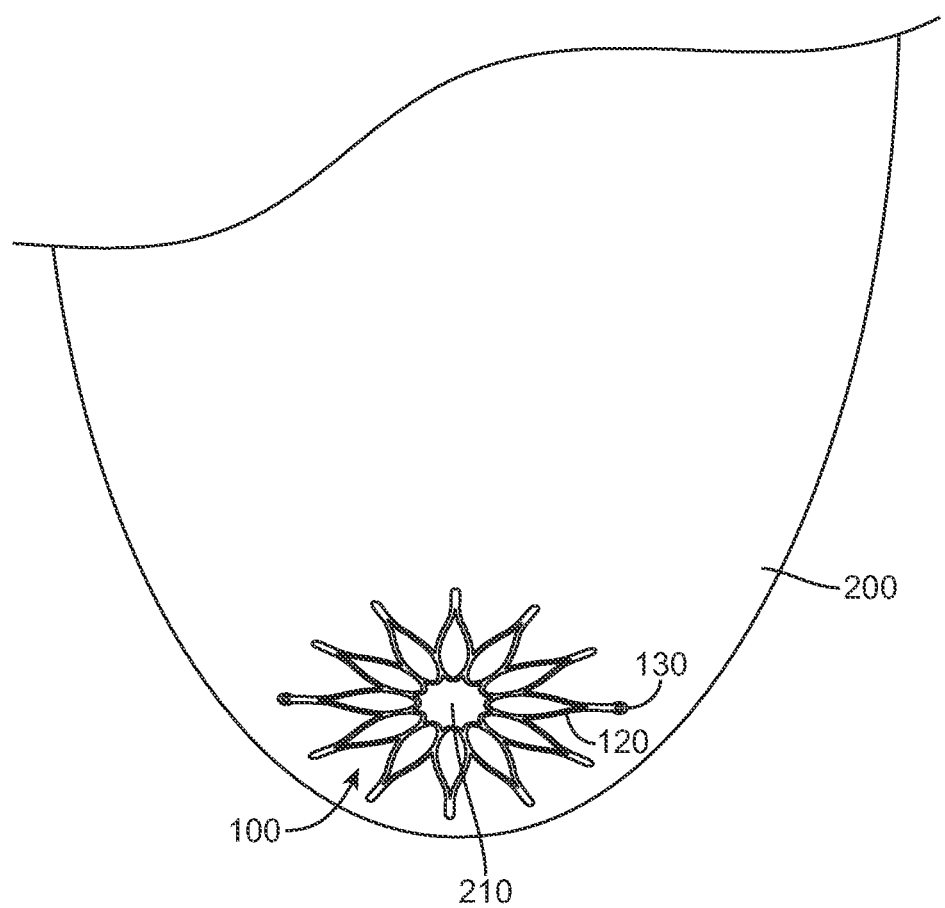

As described herein, retraction of the sheath 310 and/or the delivery device 300 with respect to the force-providing portion 120 causes the proximal end of the force-providing portion 120 to curve radially outwardly, thereby constricting the lumen formed by tissue-attachment portion 110 and maintaining the tissue-attachment portion 110 in a more constricted configuration. By constricting the tissue-attachment portion 110, the force-providing portion 120 pulls tissue (to which the tissue-attachment portion is attached) that surrounds hole 210 toward the center of the hole 210, thereby at least partially closing the hole 210, as shown in FIG. 3F, and as described hereinabove.

In some embodiments the pins 112 and may not be equidistant from the center of the hole 210 or may be oriented at varying distances from a central or center point. In such embodiments, when the force-providing portion 120 pulls tissue (to which the tissue-attachment portion is attached) that surrounds the hole 210 toward the central point of the hole 210, thereby at least partially closing the hole 210. In some embodiments different portions of the tissue may be pulled or advanced more or less toward the center point of the hole 210.

Reference is now made to FIGS. 4A-E, which illustrate respective steps of a procedure in which hole-closure device 100 is inserted into apex 210 of a subject's 200 heart using a dedicated delivery tool 400, in accordance with some embodiments. In some embodiments, the delivery tool 400 defines an inner tube 420. In some embodiments the delivery tool 400 defines an inner tube 420 and a sheath 410. In some embodiments, sheath 410 can be disposed around the inner tube 420. In some embodiments, sheath 410 can have the same or similar characteristics, function and other features as discussed above with respect to 310.

In some embodiments, delivery tool 400 is used in order to attach tissue-attachment portion 110 to the tissue surrounding the apex 210, prior to piercing and/or dilating of a hole 210 in the subject 200. In some embodiments, the piercing and/or the dilation of the hole 210 is performed while the hole-closure device 100 is already attached to the tissue surrounding the hole 210. In some embodiments, the hole-closure device 100 and corresponding tissue-attachment portion 110 may be attached to the hole 210 location prior to the creation of a hole 210 or prior to dilation of the hole 210. Thus, during the piercing and/or the dilation of the hole 210, the hole-closure device 100 can be used to close the hole 210, if appropriate.

Figure 4A:
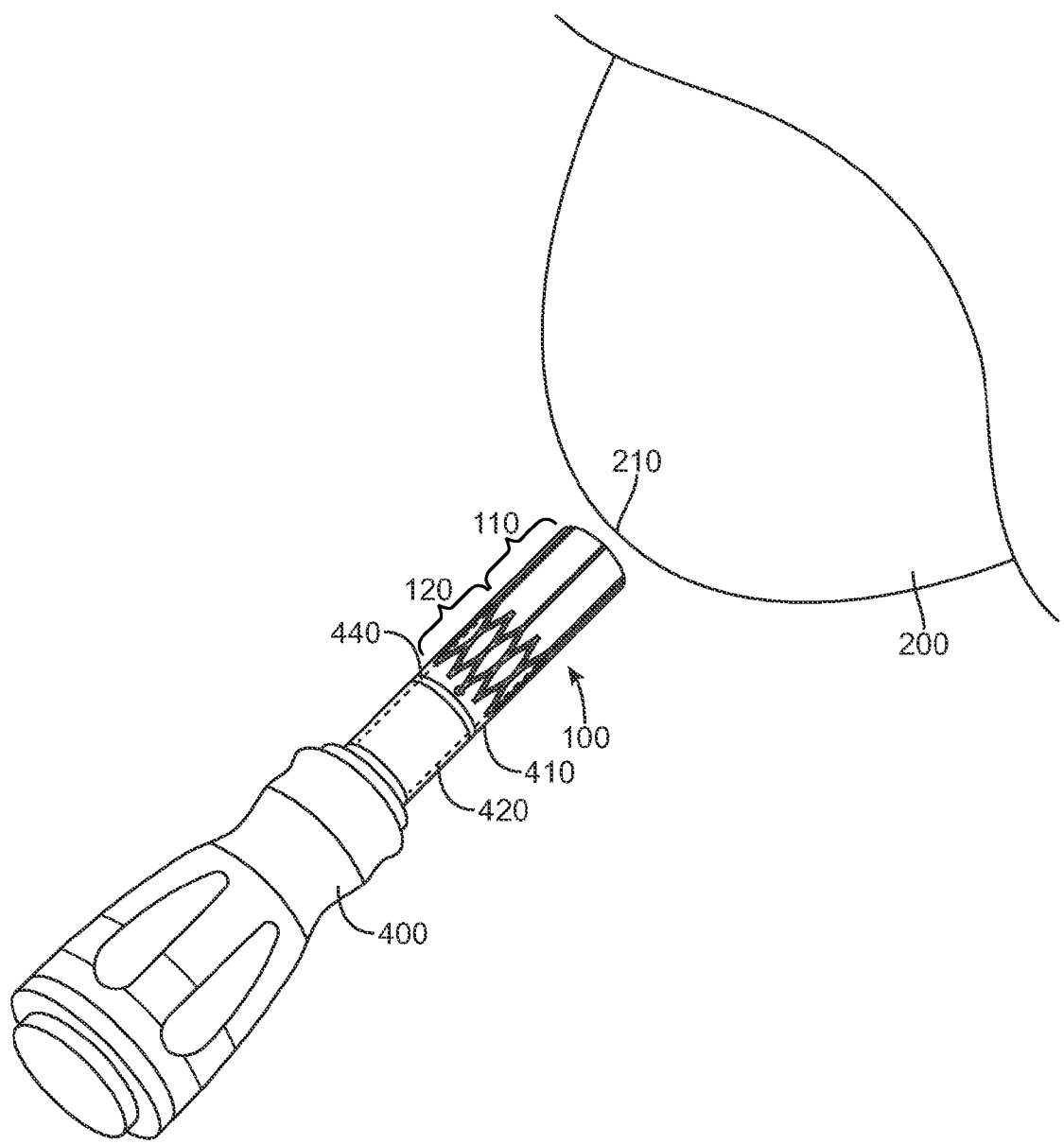
FIGS. 4A-E illustrate a procedure in which the hole-closure device is inserted into the subject, such as the apex of a subject's heart, using a dedicated delivery tool, in accordance with some embodiments.
Figure 4B:
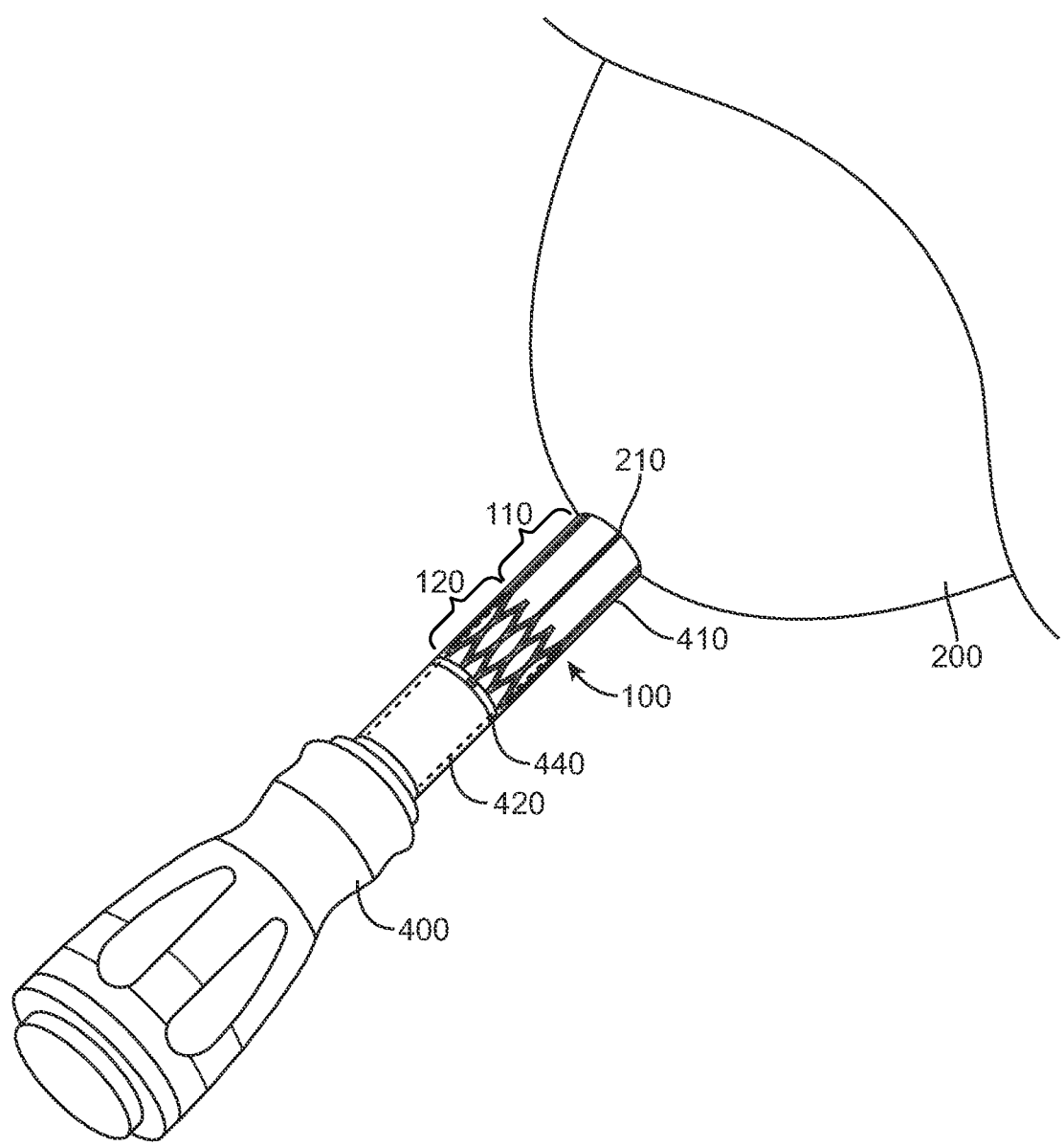

In some embodiments, as shown in FIGS. 4A-B, in a step of the procedure delivery tool 400 is advanced toward apex 210, hole-closure device 100 being disposed around inner tube 420 of the delivery device 400, and sheath 410 being disposed around the hole-closure device 100. In some embodiments, the hole-closure device 100 is constrained by inner tube 420 and sheath 410. In other embodiments the hole-closure device is constrained by inner tube 420. In some embodiments, the hole-closure device is constrained by sheath 410.

Figure 4C:
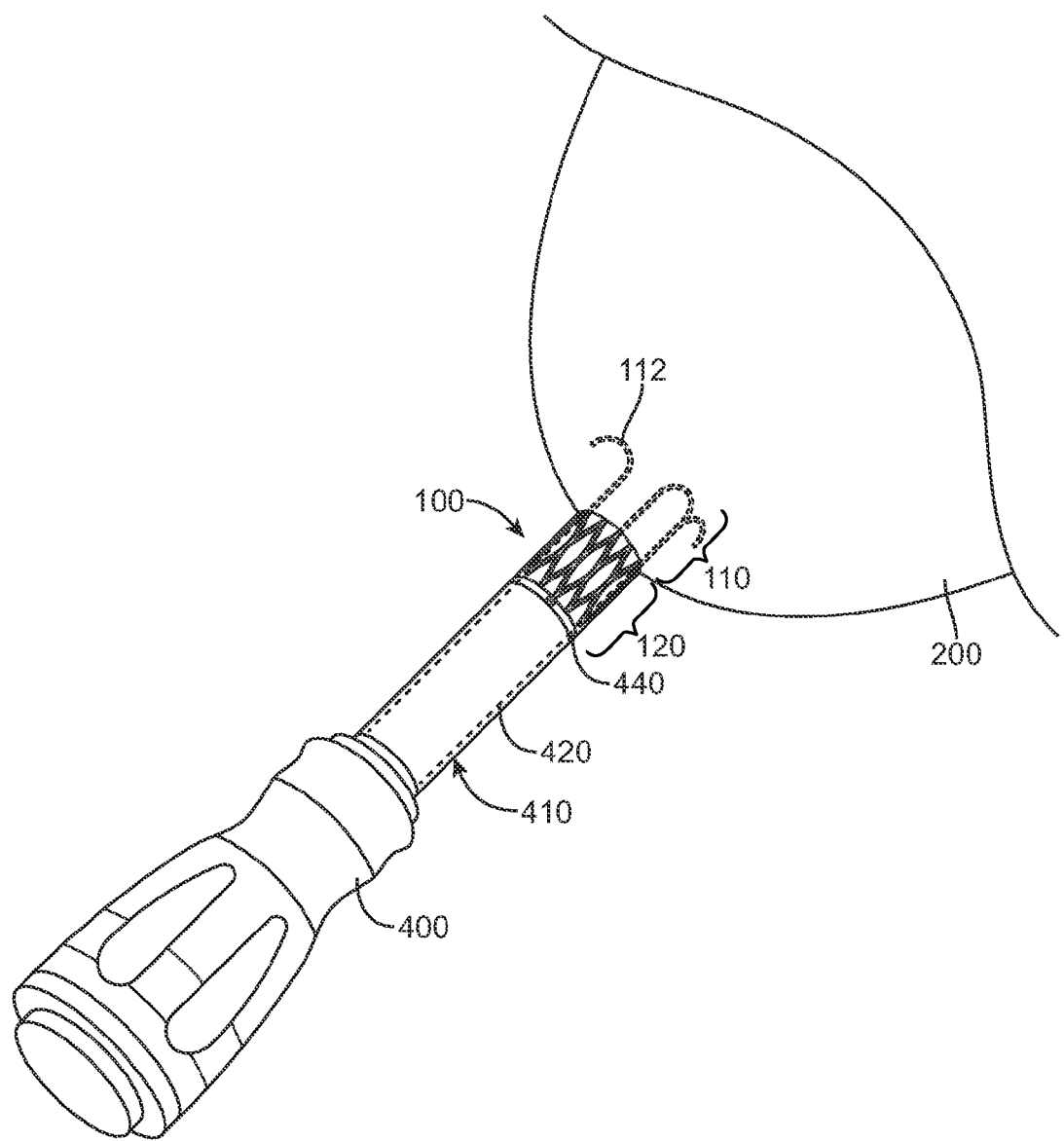

In some embodiments, when the distal end of delivery device 400 is adjacent to apex 210, tissue-attachment portion 110 of hole-closure device 100 is advanced distally with respect to distal end of the delivery tool 400, such as to attach the tissue-attachment portion 110 to tissue in the vicinity of the hole 210, as shown in FIG. 4C. In some embodiments, an advancing element 440 is used to advance the hole-closure device 100 distally with respect to the delivery tool 400. In some embodiments, an advancing element 440 is used to advance the hole-closure device 100 distally with respect to the delivery tool 400.

As shown in FIG. 4C, for some embodiments the tissue-attachment portion 110 defines pins 112, and upon being advanced distally of the sheath 410, the distal ends of the pins 112 curve radially outwardly, such that the pins 112 assume hook shapes, the pins 112 thereby becoming embedded in the tissue surrounding the hole 210. In other embodiments, the pins 112 may assume numerous other shapes, as discussed herein or as would be known to one of ordinary skill in the art.

In some embodiments, subsequent to tissue-attachment portion 110 having been attached to the tissue in the vicinity of the hole 210, a hole 210 in the subject's apex is pierced and/or dilated. In other embodiments, prior to tissue-attachment portion 110 having been attached to the tissue in the vicinity of the hole 210, a hole 210 in the apex is pierced and/or dilated. In some embodiments, the hole 210 is pierced and/or dilated by inserting a hole-piercing tool and/or a dilator via a lumen defined by inner tube 420 of delivery tool 400.

Figure 4D:
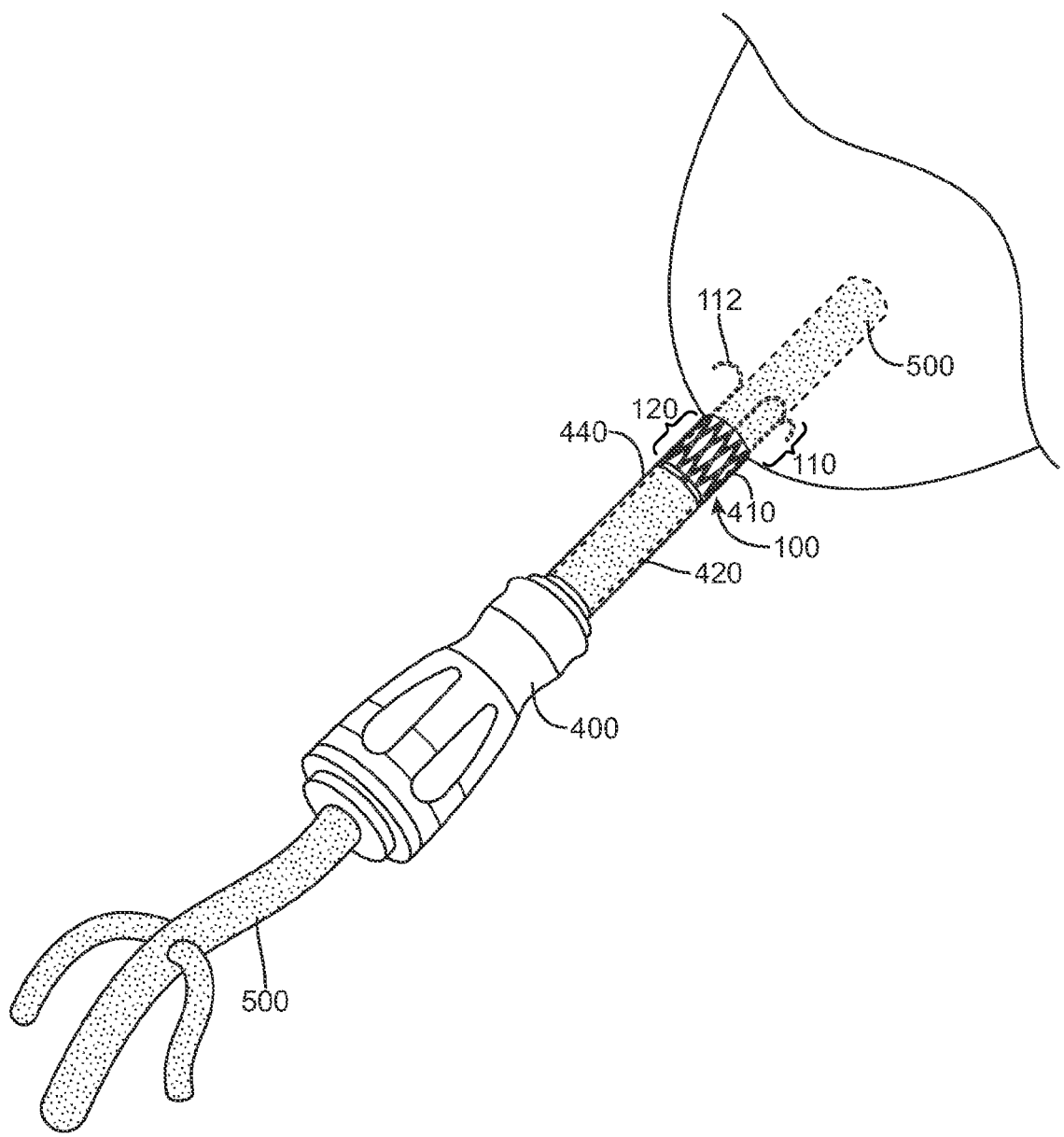

In some embodiments, a delivery tool 400, via which a transapical procedure is performed, is advanced into the subject's 200 heart, via the hole 210 in the apex, and via the lumen defined by inner tube 420 of delivery device 400. For example, FIG. 4D shows a catheter 500 that has been advanced into the subject's 200 heart, via the hole 210, and via the lumen defined by inner tube 420 of delivery tool 400. Typically, a transapical procedure is performed via catheter 500. Exemplary transapical procedures include transapical mitral valve replacement, transapical mitral valve repair, transapical aortic valve replacement, transapical aortic valve repair, left ventricular bypass, aortic cannulation and/or transapical treatment of a septal defect may be performed via the catheter. In other embodiments, in other areas and locations in the subject 200 a similar inner tube 420 may be advanced into the appropriate area of the body, providing for delivery of devices, including but not limited to catheter 500, to the appropriate area.

It is noted that FIG. 4D illustrates an embodiment where the hole-closure device 100 is disposed around inner tube 420 of delivery tool 400 while the procedure is performed via the hole 210 in the apex. However, for some embodiments, subsequent to the hole 210 in the subject's 200 tissue being pierced and/or dilated, inner tube 420 is retracted with respect to the hole-closure device 100. In some embodiments, the retraction of the inner tube 420 causes the tissue-attachment portion 110 of the hole-closure device 100 to become partially constricted or at least more constricted than before inner tube 420 was retracted, thereby pulling tissue (to which the tissue-attachment portion is attached) that surrounds the hole 210 toward the center of the hole 210, and at least partially closing the hole 210.

In some embodiments, the partial constriction of the tissue-attachment portion 110 occurs such that the hole-closure device 100 still provides a passage therethrough, such that tools (e.g., catheter 500) can be inserted via the passage. In some embodiments, the partial closure of the hole 210 resulting from the retraction of inner tube 420 provides sealing of the subject's 200 tissue with respect to the tools that are inserted via the passage. For some embodiments, subsequent to the hole 210 in the subject's 200 tissue being dilated, inner tube 420 is retracted with respect to the hole-closure device 100 and a technique is used to partially close a hole 210 in the subject's 200 atrium during a transatrial procedure.

In other embodiments, a plurality of tubes or lumens may be used to provide for a step-wise constriction of the hole 210. In some embodiments multiple tubes may be removed at various times to constrict the volume defined by the tissue-attachment portion 110 and corresponding tissue that it is attached to, such that it may become increasingly constricted as desired. In other embodiments, a single tube or multiple tubes with varying geometry may be used to provide a linear or gradual constricting of the tissue-attachment portion 110 and corresponding tissue that it is attached to. These varying geometry tubes can be configured such that as they are retracted the tissue-attachment portion 110 becomes more constricted because of the geometry of the retracted tube or tubes.

Figure 4E:
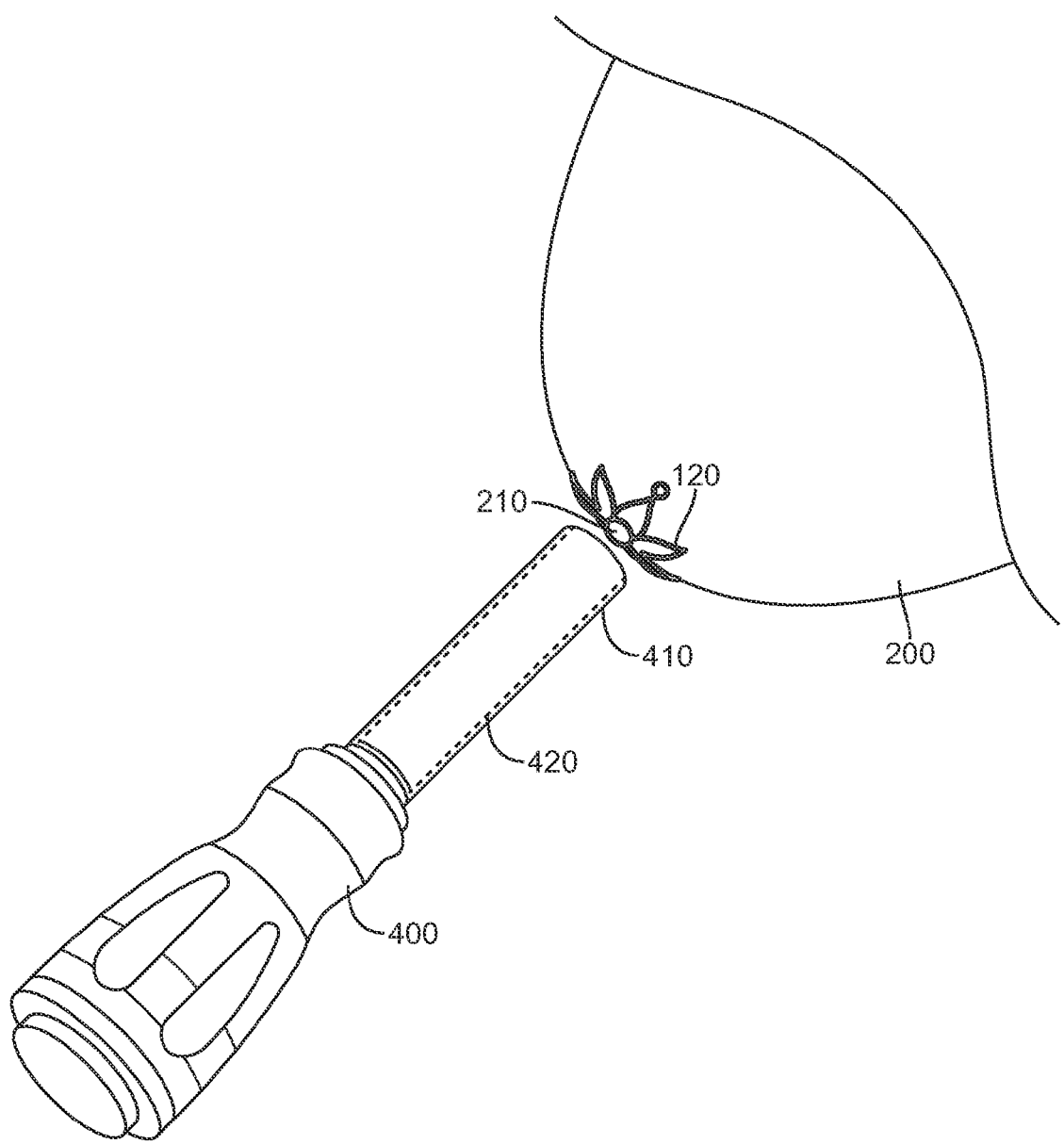

In some embodiments, subsequent to the transapical procedure having been performed, catheter 500 is removed from the subject's 200 heart by retracting the catheter 500 through the lumen defined by delivery tool 400. In some embodiments, delivery device 400 and sheath 410 are then retracted with respect to force-providing portion 120 of hole-closure device 100, as shown in FIG. 4E.

As described above, retraction of the sheath 410 with respect to the force-providing 120 portion causes the proximal end of the force-providing portion 120 to curve radially outwardly, thereby constricting the volume defined by the tissue attachment portion 110 and maintaining the tissue-attachment portion 110 in the constricted configuration. By constricting the tissue-attachment portion 110, the force-providing portion 120 pulls tissue (to which the tissue-attachment portion is attached) that surrounds the hole 210 toward the center of the hole 210 or some other point in the hole 210, thereby at least partially closing the hole 210, as described above.

It is noted that although some embodiments are described with respect to a hole 210 in the apex of a subject's 200 heart, other embodiments include using the apparatus and methods described herein to close other holes 210 in a subject's 200 body, mutatis mutandis. For example, hole-closure device 100 could be used to close a hole 210 in a subject's atrium, aorta, femoral artery, and/or a different portion of the subject's 200 body.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. An apparatus for closing a hole in a subject, the apparatus comprising:
    a hole-closure device, the hole-closure device being configured to define a constrained configuration when the hole-closure device is disposed within a delivery device, and a substantially unconstrained configuration when the delivery device has been retracted with respect to the hole-closure device, the hole-closure device comprising:
    a tissue-attachment portion comprising a plurality of pins disposed around and in parallel with a longitudinal axis of the hole-closure device, the plurality of pins being configured to achieve a distally-facing first, constrained configuration when covered by the delivery device and a second, unconstrained configuration for attachment to the subject when the delivery device has been retracted from covering the tissue-attachment portion, wherein the plurality of pins further define a lumen of the tissue-attachment portion, and
    a force-providing portion proximate the tissue-attachment portion, the force-providing portion being configured to achieve a first, constrained configuration when covered by the delivery device and a second, unconstrained configuration when the delivery device has been retracted from covering a proximal end of the force-providing portion, wherein when the proximal end of the force-providing portion is uncovered by the delivery device the force-providing portion is adapted to undergo a transition in shape to simultaneously pivot radially-outwardly and to at least partially constrict the lumen of the tissue-attachment portion by moving the plurality of pins toward the longitudinal axis of the hole-closure device.

2. The apparatus according to claim 1, wherein the force-providing portion is configured to assume a planar shape by pivoting radially-outwardly.

3. The apparatus according to claim 1, wherein the force-providing portion is configured to assume a frustoconical shape by pivoting radially-outwardly.

4. The apparatus according to claim 1, wherein the plurality of pins comprises more than three pins.

5. The apparatus according to claim 1, wherein the plurality of pins comprises less than twenty pins.

6. The apparatus according to claim 1, wherein each of the plurality of pins when in the distally-facing first configuration has a length of 2 mm to 15 mm.

7. The apparatus according to claim 1, wherein the force-providing portion is configured to assume a shape that defines a circular cross-section when in the first, constrained configuration.

8. The apparatus according to claim 1, wherein the force-providing portion is configured to prevent the hole-closure device from migrating when the hole-closure device is attached to the subject.

9. The apparatus according to claim 1, wherein when the tissue-attachment portion is in the second, unconstrained configuration each of the plurality of pins is configured to assume a hook shape by curving radially outwardly in response to retraction of the delivery device.

10. The apparatus according to claim 9, wherein when each of the plurality of pins is in the hooked shape, a length from a distal end of each pin to a center of a curved portion of each pin is between 25 percent and 50 percent of a total length of each pin.

11. The apparatus according to claim 1, wherein when the tissue-attachment portion is in the second, unconstrained configuration each of the plurality of pins is configured to assume a straight shape in response to retraction of the delivery device.

12. The apparatus according to claim 1, wherein the plurality of pins comprises more than three pins,
    wherein when the tissue-attachment portion is in the second, unconstrained configuration each of the plurality of pins is configured to assume a hook shape by curving radially outwardly in response to retraction of the delivery device,
    wherein the force-providing portion is configured to assume a shape that defines a circular cross-section when in the first, constrained configuration when covered by the delivery device,
    wherein the force-providing portion is configured to assume a planar shape by pivoting radially-outwardly when the delivery device is retracted from covering the force-providing portion of the hole-closure device, and
    wherein the lumen of the tissue-attachment portion constricts when the force-providing portion assumes the planar shape.

13. An apparatus for closing a hole and for use with a delivery device and a sheath, the apparatus comprising:
    a hole-closure device, the hole-closure device defining a tissue-attachment portion, and a force-providing portion proximate to the tissue-attachment portion,
    the hole-closure device being configured to define a constrained configuration when the hole-closure device is disposed on the delivery device and covered by the sheath, and an unconstrained configuration when the delivery device has been removed from the hole-closure device and the hole-closure device is not covered by the sheath, the tissue-attachment portion of the hole-closure device being configured to be attached to tissue that surrounds the hole within the subject, and the force-providing portion being configured to simultaneously pivot radially-outwardly and to constrict a lumen of the tissue-attachment portion by the sheath being removed from covering a proximal end of the force-providing portion, wherein the force-providing portion assumes a substantially planar shape and constricts the lumen of the tissue-attachment portion to thereby cause tissue that surrounds the hole to move inwardly to a center of the hole.

* * * * *